United States Patent
Zhan et al.

(10) Patent No.: US 12,408,896 B2
(45) Date of Patent: Sep. 9, 2025

(54) BODILY FLUID COLLECTOR AND BODILY FLUID COLLECTION METHOD

(71) Applicant: Xiamen Zeesan Biotech Co., Ltd., Fujian (CN)

(72) Inventors: Wei Zhan, Fujian (CN); Liuyi Wang, Fujian (CN); Chenchao Hu, Fujian (CN); Yi Yang, Fujian (CN)

(73) Assignee: Xiamen Zeesan Biotech Co., Ltd., Fujian (CN)

( * ) Notice: Subject to any disclaimer, the term of this patent is extended or adjusted under 35 U.S.C. 154(b) by 1158 days.

(21) Appl. No.: 16/334,181

(22) PCT Filed: Dec. 27, 2016

(86) PCT No.: PCT/CN2016/112278
§ 371 (c)(1),
(2) Date: Mar. 18, 2019

(87) PCT Pub. No.: WO2018/098876
PCT Pub. Date: Jun. 7, 2018

(65) Prior Publication Data
US 2019/0200966 A1 Jul. 4, 2019

(30) Foreign Application Priority Data
Nov. 30, 2016 (CN) .......................... 201611074757.0

(51) Int. Cl.
*A61B 10/00* (2006.01)
*B01L 3/00* (2006.01)

(52) U.S. Cl.
CPC ...... *A61B 10/0051* (2013.01); *A61B 10/0045* (2013.01); *A61B 10/0096* (2013.01); *B01L 3/502* (2013.01)

(58) Field of Classification Search
CPC ............ A61B 10/0051; A61B 10/0096; A61B 10/0045; A61B 10/007; B01L 3/502; B01L 2200/16; B65D 51/2857; B65D 51/2864
See application file for complete search history.

(56) References Cited

U.S. PATENT DOCUMENTS

| | | | |
|---|---|---|---|
| 4,761,379 A | | 8/1988 | Williams et al. |
| 5,242,660 A | * | 9/1993 | Hsei .................... B01L 3/5021 494/20 |
| 6,133,036 A | * | 10/2000 | Putcha ................. B01L 3/5082 435/2 |

(Continued)

FOREIGN PATENT DOCUMENTS

| AU | 2016262651 A1 | 12/2016 |
|---|---|---|
| CN | 101002094 A | 7/2007 |

(Continued)

OTHER PUBLICATIONS

International Search Report and Written Opinion for PCT/CN2016/112278 mailed Aug. 25, 2017, 13 pages, no translation.

(Continued)

*Primary Examiner* — Jennifer Robertson
*Assistant Examiner* — H. Q. Nguyen
(74) *Attorney, Agent, or Firm* — Myers Bigel, P.A.

(57) ABSTRACT

The present disclosure relates to the technical field of medical instruments, in particular to a bodily fluid collector and a bodily fluid collection method. The bodily fluid collector of the present disclosure comprises a collection member and a storage member having a storage chamber. Moreover, the storage chamber of the storage member may be partitioned into a first chamber for receiving a bodily fluid and a second chamber for storing a preservative product separated from each other by fitting a lower end of the collection member with the storage member, such that the isolation of the bodily fluid from the preservative product is no longer dependent on the sealing of a thin film, but only (Continued)

needs to engage the collection member with the storage member, and also such that the mixing of the bodily fluid with the preservative product is no longer dependent on the damage of the thin film by a blade, but only needs to separate the collection member from the storage member. Since the operation is simple and convenient, it is possible to realize effectively simplifying the entire bodily fluid collection process.

5 Claims, 14 Drawing Sheets

(56) References Cited

U.S. PATENT DOCUMENTS

| | | | |
|---|---|---|---|
| 8,906,310 B2 | 12/2014 | Bonecker | |
| 9,403,164 B2 | 8/2016 | Williams et al. | |
| 2002/0197738 A1* | 12/2002 | Matsumoto | A61B 10/0051 604/1 |
| 2004/0057876 A1 | 3/2004 | Wuske et al. | |
| 2005/0232813 A1 | 10/2005 | Karmali | |
| 2006/0029517 A1 | 2/2006 | Hartselle | |
| 2009/0004058 A1 | 1/2009 | Liang et al. | |
| 2009/0215159 A1* | 8/2009 | Kirby | B01L 3/502 435/287.7 |
| 2012/0325721 A1 | 12/2012 | Plante et al. | |
| 2015/0343438 A1 | 12/2015 | Williams et al. | |
| 2017/0001191 A1* | 1/2017 | Biadillah | B65D 51/2871 |
| 2018/0036733 A1* | 2/2018 | Williams | B01L 3/50825 |
| 2020/0398267 A1 | 12/2020 | Biadillah et al. | |

FOREIGN PATENT DOCUMENTS

| | | | |
|---|---|---|---|
| CN | 201188066 | | 1/2009 |
| CN | 101896276 | A | 11/2010 |
| CN | 102015482 | A | 4/2011 |
| CN | 202277840 | U | 6/2012 |
| CN | 102639246 | A | 8/2012 |
| CN | 103890163 | A | 6/2014 |
| CN | 204479337 | | 7/2015 |
| CN | 104921760 | * | 9/2015 |
| CN | 204666398 | U | 9/2015 |
| CN | 204995809 | U | 1/2016 |
| CN | 106132456 | A | 11/2016 |
| CN | 205795727 | | 12/2016 |
| CN | 206761712 | U | 12/2017 |
| EP | 2279965 | A1 | 2/2011 |
| JP | H06273418 | | 9/1994 |
| JP | 2001116739 | * | 4/2001 |
| JP | 2013167509 | | 8/2013 |
| WO | 2005086743 | A2 | 9/2005 |
| WO | 2009073152 | A1 | 6/2009 |

OTHER PUBLICATIONS

Translation of Office Action for JP Patent Application No. 2019-518042 mailed Mar. 13, 2020, 3 pages.

Extended European Search Report for EP application No. 16922730.3 mailed Nov. 12, 2019, 9 pages.

Office Action for CN application No. 201611074757.0 mailed Jan. 10, 2024, with translation, 20 pages.

* cited by examiner

BODILY FLUID COLLECTOR AND BODILY FLUID COLLECTION METHOD

RELATED APPLICATIONS

The present application is a 35 U.S.C. § 371 national phase application of PCT International Application No. PCT/CN2016/112278, filed Dec. 27, 2016, which claims priority to Chinese Patent Application No. 201611074757.0, filed Nov. 30, 2016, the disclosures of which are hereby incorporated herein by reference in their entireties.

FIELD OF THE INVENTION

The present disclosure relates to the technical field of medical instruments, in particular to a bodily fluid collector and a bodily fluid collection method.

BACKGROUND OF THE INVENTION

In the field of modern medical biology, it is usually necessary to collect bodily fluids (various secretions such as saliva and the like), in order to achieve purposes such as gene detection and the like. Moreover, in order to prolong the storage time of the collected bodily fluids, it is generally further necessary to mix the collected bodily fluids with the preservative fluid capable of prolonging the storage time before storage.

The bodily fluid collector which is an important tool for collecting bodily fluids, generally comprises a collection member and a storage member, and the collection member is used for collecting bodily fluid and guiding the bodily fluid into the storage member. After the collection amount of the bodily fluid meets the requirement, the bodily fluid and the preservative fluid are mixed in the storage member before storage. Therefore, the bodily fluid collector needs to meet the following conditions:
  (1) Before the start of collection, it should be guaranteed that the preservative fluid is in a sealed state to prevent leakage of the preservative fluid before the start of collection, which facilitates safe storage and transportation;
  (2) In the collection process, that is, after the start of collection until the collection amount meets the requirement, the body fluid should be kept in isolation from the preservative fluid in order to ensure accurate collection of bodily fluids, and prevent unnecessary harm to a collected person from leakage or backflow of the preservative product;
  (3) After the collection is completed, that is, after the collection amount of the bodily fluid meets the requirement, the bodily fluid and the preservative fluid should be mixed to prolong the storage duration of the sample.

Although the existing bodily fluid collectors can satisfy the above several conditions, they are present with the problems of complicated operation and/or high cost.

Take saliva DNA collection as an example. Saliva is a complex mixture that contains not only various proteins but also contains DNA, RNA, fatty acid, various microorganisms and the like. Moreover, in contrast to the traditional method of collecting DNA by taking blood, the saliva DNA sample collection with less intervention in human body, which may basically not cause harm and pain to the human body, is a non-invasive sample collection manner that is less prone to cause discomfort and psychological fear of a collected person, and thus is more easily accepted by the collected person. Therefore, saliva DNA collection technology has broad application prospects.

In order to prolong the storage time of the collected saliva sample DNA, the collected saliva also needs to be mixed with the preservative product capable of prolonging its storage time before storage.

The saliva collector is a bodily fluid collector that achieves saliva DNA collection. The existing saliva collectors typically comprises a funnel and a cryovial that are detachably connected. The funnel is configured to collect saliva and direct the saliva into the cryovial, and the cryovial is configured to store the collected saliva. In addition, in order to facilitate the mixing of the preservative fluid and the saliva, the saliva collector further comprises a storage cavity and a blade that are disposed on the funnel or the cryovial. The storage cavity is used for storing the preservative fluid and sealed by a film, and the blade is used for damaging the film after the saliva collection meets the requirement to mix the preservative fluid with the collected saliva.

Although the existing saliva collector which is designed to integrate the storage structure of the preservative fluid with the funnel or the cryovial may simplify the mixing process of the saliva and the preservative fluid to some extent, since it is still necessary to damage the film with the blade such as to mix the saliva with the preservative fluid after its collection is completed. Therefore, the operation is still more complicated, and problems such as a cutting failure may be caused during the process of destroying the film with the blade, which also further increases the operational difficulty. In addition, when the storage cavity is sealed with a thin film, there are also problems such as complicated process and high cost.

SUMMARY OF THE INVENTION

One technical problem to be solved by the present disclosure is that: the existing bodily fluid collector uses a thin film to seal the storage chamber that stores the preservative fluid, which results in that the operation steps of collecting the bodily fluid are very complicated.

In order to solve the aforementioned technical problem, the present disclosure provides a bodily fluid collector. The bodily fluid collector comprises a collection member and a storage member, an upper end of the collection member is open to collect bodily fluid to be detected, and the storage member has a storage chamber for storing the collected bodily fluid. Moreover, the collection member and the storage member are configured to be separably engaged such that:
  when the collection member is engaged with the storage member, a lower end of the collection member is inserted into the storage chamber and divides the storage chamber into a first chamber and a second chamber by fitting with the storage member, and the first chamber communicates with the upper end of the collection member to receive the collected bodily fluid, the second chamber is configured to store a preservative product for preserving the bodily fluid and is sealedly isolated from the first chamber to isolate the bodily fluid from the preservative product; and
  when the collection member is separated from the storage member, the lower end of the collection member is released from fitting with the storage member, and the first chamber and the second chambers communicate with each other to mix the bodily fluid and the preservative product.

Alternatively, the second chamber is located inside the first chamber in a direction parallel to a cross section of the storage chamber.

Alternatively, the storage chamber is divided into the first chamber and the second chamber by covering one of the lower end of the collection member and the storage member with the other of the lower end of the collection member and the storage member.

Alternatively, one of the lower end of the collection member and the storage member is provided with a pre-storage structure, and the other of the lower end of the collection member and the storage member is provided with a sealing structure, and the pre-storage structure comprises a pre-storage cavity for pre-storing the preservative product and an end opening located at an end of the pre-storage cavity and for receiving the preservative product into the pre-storage cavity; when the collection member is engaged with the storage member, the sealing structure cooperates with the pre-storage structure to seal the end opening, such that the first chamber is formed by a lateral outer wall of the pre-storage cavity and a lateral inner wall of the storage chamber, and such that the second chamber is formed by the pre-storage structure and the sealing structure.

Alternatively, the sealing structure covers one end of the pre-storage structure provided with the end opening to seal the end opening.

Alternatively, the sealing structure covers one end of the pre-storage structure provided with the end opening by contacting with an end surface at one end of the pre-storage structure provided with the end opening; and/or, the sealing structure covers one end of the pre-storage structure provided with the end opening by contacting with the lateral outer wall of the pre-storage cavity.

Alternatively, the sealing structure is threadedly connected or snap-fitly connected to the lateral outer wall of the pre-storage cavity.

Alternatively, the sealing structure comprises a recess with a variable cross-section, and a side wall having a variable cross-section of the recess abuts on an end surface at one end of the pre-storage structure provided with the end opening to cover the end opening; or the sealing structure comprises a gasket which is attached to and pressed against an end surface at one end of the pre-storage structure provided with the end opening to cover the end opening.

Alternatively, the pre-storage structure is disposed at a lower end of the collection member, and the end opening is disposed at a lower end of the pre-storage cavity, and a top end of the pre-storage cavity is enclosed; the sealing structure comprises a recess provided at the bottom of the storage chamber, and the recess has a cross-sectional area gradually decreasing from the top to the bottom; when the collection member is engaged with the storage member, a lower end surface of the pre-storage structure abuts against a side wall of the recess to seal the end opening.

Alternatively, the pre-storage chamber is configured to store the preservative product in a solid state, and the preservative product in a solid state is detached from the pre-storage cavity and remained in the recess under the effect of gravity when the collection member is separated from the storage member; or, the pre-storage structure is provided with a push-out mechanism, and the preservative product in a solid state is pushed by the push-out mechanism, detached from the pre-storage cavity and remained in the recess when the collection member is separated from the storage member.

Alternatively, the pre-storage structure is disposed on the storage member and located in the storage chamber, and the end opening is located at an upper end of the pre-storage cavity; the sealing structure comprises a sealing gasket provided at a lower end of the collection member; the sealing gasket is attached to and pressed against an upper end surface of the pre-storage structure to enclose the end opening when the collection member is engaged with the storage member.

Alternatively, the pre-storage structure comprises a pre-storage tube, and the pre-storage cavity is a cavity of the pre-storage tube; or the pre-storage structure comprises a pre-storage block having a groove, and the pre-storage cavity is a cavity of the groove.

Alternatively, the collection member comprises a conduit connected between an upper end and a lower end of the collection member, and the upper end of the conduit at least partially communicates with the upper end of the collection member, the lower end of the conduit is enclosed, and the side wall of the conduit is provided with an opening; the conduit protrudes into the storage chamber so that the collected bodily fluid flows into the first chamber via the opening when the collection member is engaged with the storage member.

Alternatively, a cross-section of the upper end of the collection member is in the shape of an obround hole.

Alternatively, the collection member is provided with a liquid squeezing tank for squeezing a sampling member with the bodily fluid and draining the squeezed bodily fluid into the first chamber.

Alternatively, the bodily fluid collector further comprises a blockage, which is detachably connected to an upper opening of the storage chamber, such that the blockage seals the upper opening of the storage chamber when the blockage is fitted with the upper opening of the storage chamber.

Alternatively, the blockage is also connectable to a lower end of the storage member.

Another aspect of the present disclosure also provides a bodily fluid collection method based on the bodily fluid collector of the present disclosure. The bodily fluid collection method comprises the following steps in sequence:

collecting a bodily fluid with the collection member engaged to the storage member, such that the bodily fluid flows into the first chamber isolated from the second chamber; and separating the collection member and the storage member when a collection amount of the bodily fluid meets the requirement, such that the first chamber communicates with the second chamber to mix the bodily fluid with the preservative product.

According to the bodily fluid collector of the present disclosure, the storage chamber of the storage member may be partitioned into a first chamber and a second chamber isolated from each other by fitting a lower end of the collection member with the storage member. That is, two temporary independent cavities may be formed by engaging the collection member with the storage member. This allows that the isolation of the bodily fluid from the preservative product is no longer dependent on the sealing of a thin film, but only needs to engage the collection member with the storage member, and also allows that the mixing of the bodily fluid with the preservative product is no longer dependent on the damage of the thin film by a blade, but only needs to separate the collection member from the storage member. Since the operation is simple and convenient, it is possible to realize effectively simplifying the entire bodily fluid collection process.

Other features of the present disclosure and advantages thereof will become explicit by means of the following detailed descriptions of exemplary embodiments of the present disclosure with reference to the drawings.

BRIEF DESCRIPTION OF THE ACCOMPANYING DRAWINGS

In order to more clearly explain the embodiments of the present disclosure or the technical solutions in the prior art, a brief introduction will be given below for the drawings required to be used in the description of the embodiments or the prior art. It is obvious that, the drawings illustrated as follows are merely some of the embodiments of the present disclosure. For those skilled in the art, they may also acquire other drawings according to such drawings on the premise that no inventive effort is involved.

Figure 1:
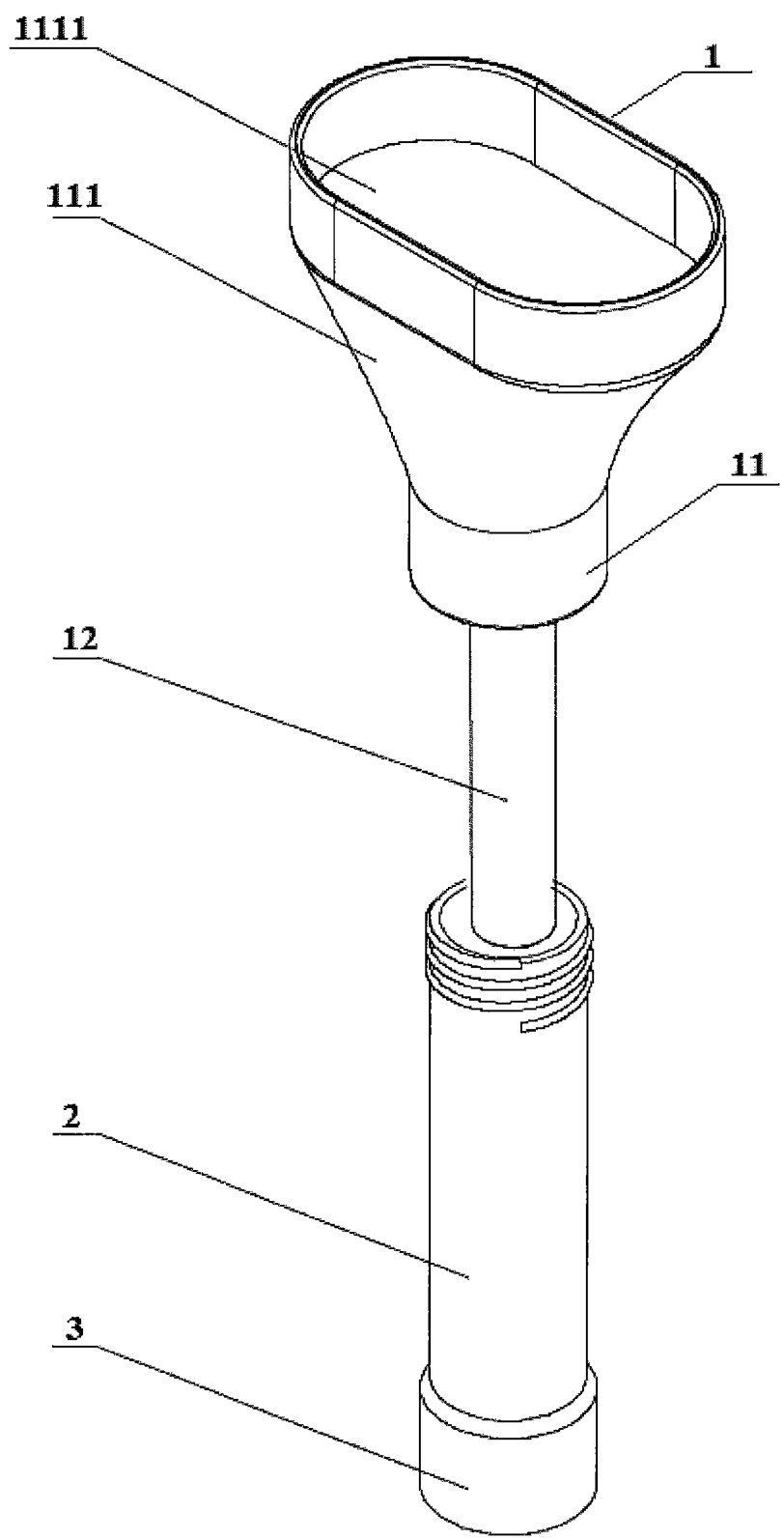
FIG. 1 shows a perspective structural view of the bodily fluid collector according to a first embodiment of the present disclosure when the collection member and the storage member are not in an engaged state.

In the drawings:
1. collection member;
11. collection body; 111. funnel; 1111. collection port; 1112. collection cavity; 1113. liquid squeezing tank; 112. conduit; 1121. opening;
12. pre-storage structure; 12*a*. pre-storage tube; 12*b*. pre-storage block; 121. pre-storage cavity; 122. end opening;
13. sealing structure; 13*a*. recess; 13*b*. sealing gasket;
14. support portion;
2. storage member; 21. storage chamber; 211. first chamber; 212. second chamber;
3. blockage;
4. cotton swab.

DETAILED DESCRIPTION OF THE PREFERRED EMBODIMENTS

Next, the technical solution in the embodiments of the present disclosure will be explicitly and completely described in combination with the drawings in the embodiments of the present disclosure. Apparently, the described embodiments are merely part of the embodiments of the present disclosure, rather than all the embodiments. The following descriptions of at least one exemplary embodiment which are in fact merely descriptive, by no means serve as any delimitation on the present disclosure as well as its application or use. On the basis of the embodiments of the present disclosure, all the other embodiments acquired by a person skilled in the art on the premise that no inventive effort is involved fall into the protection scope of the present disclosure.

The techniques, methods, and apparatuses known to a common technical person in the relevant art may not be discussed in detail, but where appropriate, techniques, methods, and apparatuses should be considered as part of the granted description.

In the description of the present disclosure, it is necessary to understand that, such wordings as "first" and "second" which are configured to define the parts, are only intended to facilitate distinguishing the corresponding parts. Unless otherwise specified, the aforementioned wordings do not have particular meanings, and thus cannot be understood as limiting the protection scope of the present disclosure.

Further, in the description of the present disclosure, the azimuth or positional relations indicated by such azimuth terms as "front, rear, up, down, left, right", "transverse, vertical, perpendicular, horizontal" and "top, bottom", are based on the azimuth or positional relations when the bodily fluid collector is in normal use. The azimuth terms "within" and "outside" mean the interior and exterior relative to the contour of various members themselves.

FIGS. 1-14 show four embodiments of the bodily fluid collector of the present disclosure. With reference to FIGS. 1-14, the bodily fluid collector provided by the present disclosure comprises a collection member 1 and a storage member 2. An upper end of the collection member 1 is open to collect a bodily fluid to be detected, and the storage member 2 has a storage chamber 21 for storing the collected bodily fluid. Moreover, the collection member 1 and the storage member 2 are configured to be separably engaged such that:

When the collection member 1 is engaged with the storage member 2, a lower end of the collection member 1 is inserted into the storage chamber 21 and divides the storage chamber 21 into a first chamber 211 and a second chamber 212 by fitting with the storage member 2, the first chamber 211 communicates with the upper end of the collection member 1 to receive the collected bodily fluid, and the second chamber 212 is configured to store a preservative product for preserving the bodily fluid and is sealedly isolated from the first chamber 211 to separate the bodily fluid from the preservative product.

When the collection member 1 is separated from the storage member 2, the lower end of the collection member 1 is released from fitting with the storage member 2, such that the first chamber 211 and the second chambers 212 communicate with each other so that the bodily fluid and the preservative product is mixed.

The bodily fluid collector according to the present disclosure, in which the isolation of the bodily fluid from the preservative product is no longer dependent on the sealing of the thin film, but is realized by the first chamber 211 for receiving the bodily fluid and the second chamber 212 for storing the preservative product that are partitioned by fitting the lower end of the collection member 1 with the storage member 2. Since the fit between the lower end of the collection member 1 and the storage member 2 may be formed after the collection member 1 is engaged with the storage member 2, and the fit between the lower end of the collection member 1 and the storage member 2 may also be released in the process of separating the collection member 1 from the storage member 2, based on the bodily solution collector according to the present disclosure, it is only necessary to engage and separate the collection member 1 and the storage member 2, such as to effectuate sealing the preservative product before the start of the collection, isolating the bodily fluid from the preservative product in the collection process and mixing the bodily fluid with the preservative product after the collection is completed.

In the present disclosure, "in the collection process" means "after the start of collection until the collection amount meets the requirement" and "after the collection is completed" means "after the collection amount of the bodily fluid meets the requirement", and "the collection amount meets the requirement" normally means that the collection amount reaches a predetermined amount, but for some special circumstances, for example when the collected person indeed cannot provide a predetermined amount of bodily fluid, it may be also considered that the requirement has been basically met when there is certain gap between a collection amount and a predetermined amount.

It can be seen that, compared with the prior art in which it is necessary to seal the preservative fluid with a thin film in advance and afterwards also necessary to damage the thin film with a blade, the present disclosure can effectively simplify the entire bodily fluid collection process and improve the bodily fluid collection efficiency. Moreover, since the film sealing process may be omitted, the machining process of the bodily fluid collector according to the present disclosure is relatively simple, so that the machining cost may be saved. At the same time, since the mixing of the bodily fluid with the preservative product is not dependent on the blade, it can also avoid the occurrence of such a phenomenon that the bodily fluid cannot be mixed with the preservative product resulting from a cutting failure of the blade and the like, and improve the operational reliability of the bodily fluid collector.

In the present disclosure, the preservative product comprises a preservative fluid in a liquid state or a preservative tablet A in a solid state. Also in other words, by using the bodily fluid collector of the present disclosure, it is possible to effectuate mixing the preservative fluid with the bodily fluid, and it is also possible to effectuate mixing the preservative tablet A with the bodily fluid. Both the preservative fluid and the preservative tablet A are used for a mixed reaction with the bodily fluid to effectuate prolonging a storage duration of the sample. Among them, since the preservative fluid is a liquid preservative product, it has a high requirement for the transport process; since the preservative tablet A is a solid preservative product, it is more convenient for transport. Further, for the same amount of bodily fluid, the volume of the desired preservative tablet A may be less than that of the desired preservative fluid.

According to the present disclosure, one of the lower end of the collection member 1 and the storage member 2 may plug the other to partition the storage chamber 21 into a first chamber 211 and a second chamber 212, i.e. the storage chamber 21 is partitioned into the first chamber 211 and the second chamber 212 by plugging fit of the lower end of the collection member 1 and the storage member 2. Alternatively, according to the present disclosure, one of the lower end of the collection member 1 and the storage member 2 may also cover the other to partition the storage chamber 21 into the first chamber 211 and the second chamber 212, that is, the storage chamber 21 is partitioned into a first chamber 211 and a second chamber 212 by covering one of the lower end of the collection member 1 and the storage member 2 with the other of the lower end of the collection member 1 and the storage member 2. Among them, the covering manner is preferred, because relative to the plugging fit manner, the covering manner may reduce the interference with the preservative product. This will be further explained below.

In addition, in the first chamber 211 and the second chamber 212 formed by fitting the collection member 1 with the storage member 2, the second chamber 212 may be located below the first chamber 211. Also in other words, in the collection process, the preservative product is located below the bodily fluid. However, more preferably, the positional relationship between the first chamber 211 and the second chamber 212 is provided such that: the second chamber 212 is located inside the first chamber 211 in a direction parallel to a cross section of the storage chamber 21 (hereinafter all simply referred to in a way such that the second chamber 212 is located inside the first chamber 211).

For the circumstance that the second chamber 212 is located below the first chamber 211, since the preservative product (especially the preservative fluid) is added in advance, the preservative product has to first pass through the first chamber 211 for receiving a bodily fluid such as to be able to enter the second chamber 212, so that the preservative product may inevitably be remained within the first chamber 211, which causes contamination to the first chamber 211. Therefore, on the one hand, this results in unnecessary loss of the preservative product; on the other hand, the preservative product remaining in the first chamber 211 may be mixed with the bodily fluid flowing into the first chamber 211 during the collection process, resulting in undesired mixing the bodily fluid with the preservative product during the collection process; on the other hand, residual preservative product in the first chamber 211 may also further contaminate the collection member 1. Since the collection member 1 is directly in contact with the collected person, it may also cause chemical contamination to the collected person and cause damage to the collected person, and lead to safety accidents and affect the use experience. Further, by providing the second chamber 212 inside the first chamber 211, it is possible to allow that the preservative product is added to the second chamber 212 in advance without having to pass through the first chamber 211. Therefore, the configuration manner can avoid a series of problems caused by the aforementioned configuration that the second chamber 212 is disposed below the first chamber 211 as mentioned above, and further ensure that the bodily fluid and the preservative product are better isolated until the collection is completed, thereby saving the preservative product and improving the operational safety and the user experience. Moreover, with respect to the case where the second chamber 212 is located below the first chamber 211, by providing the second chamber 212 inside the first chamber 211, it is favorable to allow that both the bodily fluid and the preservative product are located at the bottom of the storage member 2 before being mixed, and it is possible to further facilitate mixing the bodily fluid with the preservative product, and more facilitate adequately mixing both of them, and improving the collection quality of the sample.

As one embodiment of the present disclosure, one of the lower end of the collection member 1 and the storage member 2 is provided with a pre-storage structure 12, and the other of the lower end of the collection member 1 and the storage member 2 is provided with a sealing structure 13, and the pre-storage structure 12 comprises a pre-storage cavity 121 for pre-storing the preservative product and an end opening 122 located at an end of the pre-storage cavity 121 and used for receiving the preservative product into the pre-storage cavity 121. When the collection member 1 is engaged with the storage member 2, the sealing structure 13 cooperates with the pre-storage structure 12 to seal the end opening 122, such that the first chamber 211 is formed by a lateral outer wall of the pre-storage cavity 121 and a lateral inner wall of the storage chamber 21, and such that the second chamber 212 is formed by the pre-storage structure 12 and the sealing structure 13.

Based on this embodiment, on one hand, the bodily fluid collector of the present disclosure may conveniently form the first chamber 211 and the second chamber 212 internally and externally provided and isolated from each other as mentioned above, by fitting the pre-storage structure 12 with the sealing structure 13 when the collection member 1 is engaged with the storage member 2. This allows that the preservative product may be in a sealed state before the start of the collection to ensure safe transport and storage, and allows that the bodily fluid and the preservative product may be in an isolated state in the collection process to ensure accurate collection and safe collection. On the other hand, in the bodily fluid collector of the present disclosure the first chamber 211 is conveniently communicated with the second chamber 212 when the collection member 1 is separated from the storage member 2, so that it may be realized that the bodily fluid is rapidly mixed with the preservative product after the collection is completed, and the storage duration of the sample is prolonged.

In the aforementioned embodiment, the fit between the sealing structure 13 and the pre-storage structure 12 may be a plugging fit, i.e. the sealing structure 13 is inserted into the pre-storage cavity 121 through the end opening 122 to contact with the inner wall of the pre-storage cavity 121 so as to seal the end opening 122; and may also be a covering fit, i.e. the sealing structure 13 covers one end of the pre-storage structure 12 provided with the end opening 122 to seal the end opening 122. In order to reduce the interference of the sealing structure 13 with the preservative product pre-stored in the pre-storage cavity 121, the fitting manner between the sealing structure 13 and the pre-storage structure 12 is preferably a covering fit manner, because there is no need to insert the sealing structure 13 into the pre-storage cavity 121 when the sealing of the end opening 122 is realized on the basis of a covering fit. Accordingly, by using a covering fit manner, it is not only possible to reduce the contamination of the preservative product (especially the preservative fluid) by the dust and the like on the sealing structure 13, and favorable to maintain the purity and utility of the preservative product, but also possible to avoid that the volume of the pre-storage cavity 121 is occupied due to the insertion of the sealing structure 13, and more favorable for the storage of the preservative product.

Further, in order to effectuate covering one end of the pre-storage structure 12 provided with the end opening 122, the sealing structure 13 in the aforementioned embodiment may be in contact with an end surface at an end of the pre-storage structure 12 provided with the end opening 122, and/or the sealing structure 13 may be in contact with the lateral outer wall of the pre-storage cavity 121. The "contact" here is determined by the fact that the sealing of the end opening 122 can be realized.

As an embodiment in which the sealing structure 13 is in contact with the lateral outer wall of the pre-storage cavity 121 such as to cover one end of the storage structure 12 provided with the end opening 122, the sealing structure 13 may only be in contact with the lateral outer wall of the pre-storage cavity 121, or may also contact with the lateral outer wall of the pre-storage cavity 121 and the end surface at one end of the pre-storage structure 12 provided with the end opening 122 at the same time. Such sealing structure 13 can cover the end opening 122 to effectuate covering one end of the pre-storage structure 12 provided with the end opening 122, and effectuate sealing the end opening 121. Further, the contact of the sealing structure 13 with the lateral outer wall of the pre-storage cavity 121 may be realized by threaded connection between the sealing structure 13 and the lateral outer wall of the pre-storage cavity 121, or may also be realized by a snap-fit connection between the sealing structure 13 and the lateral outer wall of the pre-storage cavity 121.

Moreover, as an embodiment in which the sealing structure 13 is in contact with the end surface at one end of the pre-storage structure 12 provided with an end opening 122 such as to cover one end of the pre-storage structure 12 provided with the end opening 122, the sealing structure 13 may only be in contact with the end surface at one end of the pre-storage structure 12 provided with an end opening 122, so that the sealing structure 13 can cover the end opening 122 such as to effectuate pressing and covering one end of the pre-storage structure 12 provided with an end opening 122. Here, the contact between the sealing structure 13 and the end surface at one end of the pre-storage structure 12 provided with an end opening 122 comprises both the case of contacting with an entire end surface at one end of the pre-storage structure 12 provided with an end opening 122, and the case of locally contacting with the end surface at one end of the pre-storage structure 12 provided with an end opening 122. Also in other words, it is only necessary to at least partially contact the sealing structure 13 with the end surface at one end of the pre-storage structure 12 provided with an end opening 122 such as to effectuate sealing the end opening 122.

In the present disclosure, the sealing structure 13 may comprise a recess 13a with a variable cross-section, and may also comprise a sealing gasket 13b, and a side wall having a variable cross-section of the recess 13a may be attached to and pressed against an end surface at one end of the pre-storage structure 12 provided with the end opening 122 such as to cover on the end opening 122, and the sealing gasket 13b may be directly attached to and pressed against an end surface at one end of the pre-storage structure 12 provided with the end opening 122 such as to cover on the end opening 122, to effectuate sealing the end opening 122.

In addition, in the aforementioned embodiment, the pre-storage structure 12 may be a pre-storage tube 12a, and may also be a pre-storage block 12b provided with a groove thereon. When the pre-storage tube 12a is used, the cavity thereof may serve as a pre-storage cavity 121, and an end opening of the cavity is as an end opening 122; and when the pre-storage block 12b is used, a cavity of the groove may serve as a pre-storage cavity 121, and an opening of the groove is as an end opening 122. Moreover, since the volume of the cavity of the pre-storage tube 12*a* is generally greater than the volume of the groove of the pre-storage block 12*b*, the pre-storage tube 12*a* is more suitable for pre-storing a preservative fluid having a larger occupied volume, and the pre-storage block 12*b* is more suitable for pre-storing a preservative tablet B having a smaller occupied volume. Further, both the pre-storage tube 12*a* and the pre-storage block 12*b* may be fitted with the aforementioned various sealing structures.

FIGS. 1-14 show four embodiments of the bodily fluid collector of the present disclosure. In these four embodiments, the bodily fluid collectors are all formed into such two temporary independent cavities as the first chamber 211 and the second chamber 212 by covering the pre-storage structure 12 with the sealing structure 13, and the differences mainly lie in different specific structures and covering manners of the pre-storage structure 12 and the sealing structure 13. Therefore, the following only focuses on description of the first embodiment, and the other three embodiments only describe their main differences from the first embodiment, with the undescribed portions that may be understood with reference to the first embodiment. Moreover, for the purpose of convenient description, the collected bodily fluid as saliva is only taken as example for illustration. Also in other words, in these four embodiments, although the bodily fluid collector serves as a saliva collector, a person skilled in the art should understand that the bodily collector of the present disclosure may also actually collect other bodily fluids.

Next, the present disclosure will be further illustrated in combination with these four embodiments.

FIGS. 1-4 show a first embodiment of the bodily fluid collector according to the present disclosure. In the first embodiment, the preservative fluid as a preservative product is taken as an example.

As shown in FIGS. 1-4, in the first embodiment, the bodily fluid collector comprises a collection member 1, a storage member 2, and a blockage 3, and both the collection member 1 and the blockage 3 are detachably connected with the storage member 2. The collection member 1 which is connected to the storage member 2 before the start of the collection and in the collection process, is not only used for collecting the saliva and guiding the saliva into the storage member 2, but also used for sealing and isolating the preservative fluid before the start of the collection and in the collection process. The blockage 3 is used for sealing the storage member 2 after the completion of the collection, so as to facilitate subsequent transport and storage and prevent leakage of the sample.

Figure 2:
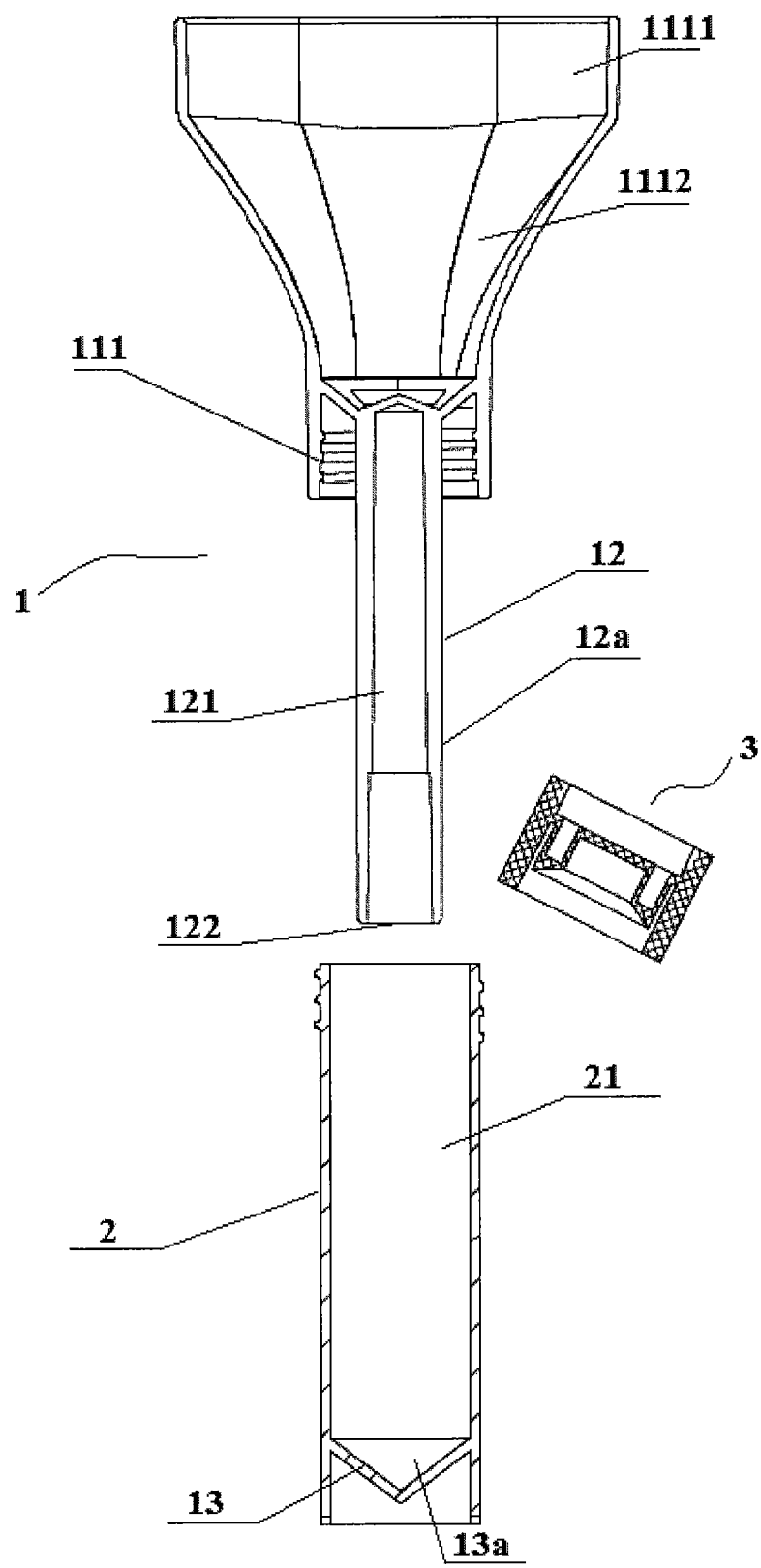
FIG. 2 shows an exploded structural view of FIG. 1.

As shown in FIG. 1 and FIG. 2, in this embodiment, the storage member 2 is a hollow circular tube, whose hollow cavity is used as a storage chamber 21, with an upper end thereof open and a lower end enclosed, so that the saliva can enter the storage chamber 21 from the upper opening of the storage chamber 21 for storage. Moreover, as can be known from FIG. 2, in this embodiment, the bottom wall of the storage chamber 21 is recessed downward to form a recess 13*a* at the bottom of the storage chamber 21, and the recess 13*a* presents an inverted conical shape with a cross-sectional area gradually decreasing from the top to the bottom. In this embodiment, the recess 13*a* serves as a sealing structure 13 for partitioning the storage chamber 21 into two temporary independent cavities internally and externally provided, i.e. the first chamber 211 and the second chamber 212 as mentioned above, by fitting with the pre-storage structure 12 provided at the lower end of the collection member 1. This will be further described below.

As can be known from FIG. 1, the upper portion of the lateral outer wall of the storage chamber 21 is provided with an external thread for effectuating detachably connecting the storage member 2 with the collection member 1 and the blockage 3, so that the engagement of the collection member 1 or the blockage 3 with the storage member 2 may be conveniently realized by tightening the collection member 1 or the blockage 3 onto the storage member 2. Of course, the engagement manner of the collection member 1 and the blockage 3 with the storage member 2 is not limited to a threaded connection manner, and it falls within the protection scope of the present disclosure, as long as it is possible to effectuate detachably connecting the collection member 1 and the blockage 3 with the storage member 2 and ensure that the blockage 3 seals the upper opening of the storage chamber 21.

In addition, in order to facilitate determining whether the collection amount of the saliva reaches a predetermined amount, it is also possible to provide a scale line (not shown in the figures) on the side wall of the storage chamber 21, so that it may be judged that the collection amount of the saliva has reached a predetermined amount when the level of the collected saliva reaches the height of the scale line.

Figure 3:
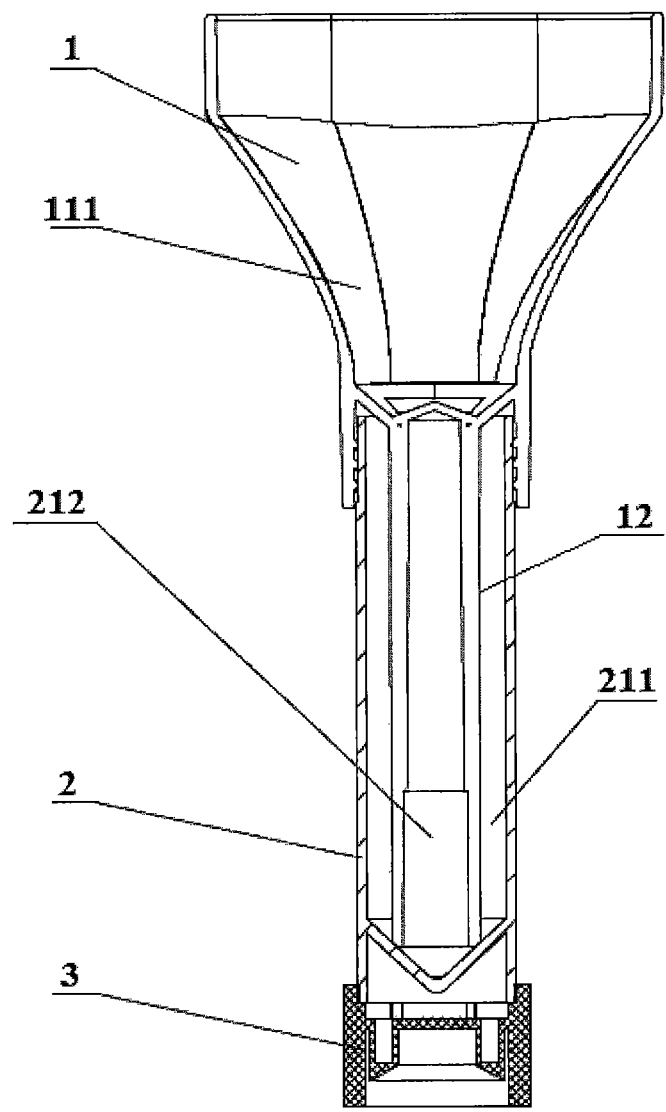
FIG. 3 shows a cross-sectional view of the bodily fluid collector shown in FIG. 1 when the collection member and the storage member are in an engaged state.

As shown in FIGS. 1-3, in this embodiment, the collection member 1 comprises a collection body 11 and a pre-storage tube 12*a* connected to the lower portion of the collection body 11. The collection body 11 is configured to collect the saliva. The pre-storage tube 12*a* serves as a pre-storage structure 12, which is configured to pre-store the preservative fluid, and to cooperate with the recess 13*a* on storage member 2, so as to partition the storage chamber 21 into such two independent cavities internally and externally provided as the first chamber 211 and the second chamber 212.

Specifically, as shown in FIG. 2, the collection body 11 of this embodiment comprises a funnel 111. The funnel 111 has a collection cavity 1112 that is open both at the top and the bottom. The upper end of the collection cavity 1112 is the upper end of the collection member 1, which is open to form a collection port 1111 for receiving the saliva to be detected, so that the collection cavity 1112 can collect the saliva to be detected. The inner wall at the lower end of the collection cavity 1112 is provided with an internal thread for mating with the external thread on the storage member 2 to detachably connect the collection member 1 with the storage member 2. As shown in FIG. 1, a cross-sectional shape of the collection port 1111 of this embodiment is in the shape of an obround hole. Since the obround hole conforms more to the profile of the mouth of the collected person, the collection port 1111 may be better attached to the mouth of the collected person. Therefore, it is not only possible to improve the operational comfort of the collector, but also possible to effectively prevent the outflow of the saliva via the collection port 1111. The funnel 111 is preferably made of an environmentally friendly plastic material for facilitating extrusion and recycling.

As shown in FIGS. 1-3, the pre-storage tube 12*a* of this embodiment is connected to the lower part of the funnel 111. Specifically, the pre-storage tube 12*a* is connected to the inner wall of the collection cavity 1112, and the lower end of the pre-storage tube 12*a* extends to below the lower end of the funnel 111. Therefore, it should be noted that, the lower end of the pre-storage tube 12*a* is the lower end of the collection member 1.

Since the saliva needs to enter the storage chamber 21 through the collection cavity 1112 in the collection process, the collection cavity 1112 also needs to communicate with the storage chamber 21. Further, in order to achieve the communication between the collection cavity 1112 and the storage chamber 21, in this embodiment, an outflow port is further provided at the connection of the pre-storage tube 12*a* and the inner wall of the collection cavity 1112. The outflow port communicates with the portion of the collection cavity 1112 located above the pre-storage tube 12*a* and the portion thereof located below the pre-storage tube 12*a*, such that the outflow port may communicates with the storage chamber 21 and the collection port 1111 (i.e. the upper end of the collection member 1) so that the saliva may flow into the storage member 2 via the collection member 1, when the collection member 1 is connected onto the storage member 2.

The outflow port may be an entire annular opening. For example, an annular connecting piece may be provided between the pre-storage tube 12*a* and the inner wall of the collection cavity 1112. The connecting piece connects the pre-storage tube 12*a* onto an entire inner wall of the collection cavity 1112 situated at the same height, and an annular opening is opened on the annular piece as an outlet. Alternatively, the outflow port may also consist in several local openings that are spacedly provided. For example, two spaced connecting pieces in a sector shape may be provided between the pre-storage tube 12*a* and the inner wall of the collection cavity 1112, and the two connecting pieces connect the pre-storage tube 12*a* to the local inner wall of the collection cavity 1112 situated at the same height, so that two outflow ports in a sector shape are formed between the two connecting pieces and the inner wall of the collection cavity 1112. Of course, the shape and number of the connecting pieces may be set according to actual conditions, as long as it is ensured to form the outflow ports that can communicate the collection cavity 1112 with the storage chamber 21. Moreover, a plurality of outflow ports in a sector shape that are spacedly provided may produce a better guiding effect, and facilitate that the saliva more smoothly flows into the storage chamber 21.

In addition, as can be known from FIG. 2, in this embodiment, the pre-storage tube 12*a* is also a hollow circular tube having a pre-storage cavity 121 for pre-storing the preservative fluid and an end opening 122 for receiving the preservative fluid into the pre-storage cavity 121. The pre-storage cavity 121 is a cavity of the pre-storage tube 12*a*, a top end thereof is enclosed and a lower end is open, and the end opening 122 is the lower end opening of the pre-storage cavity 121, which allows that the preservative fluid may enter the pre-storage cavity 121 via the end opening 122 for storage. On such basis, prior to the assembly of the collection member 1 and the storage member 2, the collection member 1 may be first inverted so that the end opening 122 faces upwards, and the preservative fluid is poured into the pre-storage cavity 121 (cavity of the pre-storage tube 12*a*) via the end opening 122, so that the preservative fluid is stored in the pre-storage cavity 121 in advance, so as to sequentially effectuate sealing and isolating the preservative fluid by screwing the storage member 2 onto the funnel 111. The top end of the pre-storage cavity 121 is provided to be enclosed, so that it is not only possible to prevent the leakage of the preservative fluid from the pre-storage cavity 121 when the collection member 1 is inverted, but also possible to allow that the saliva only flows into the storage chamber 21 via the outflow port in the collection process, thereby preventing that the saliva enters the pre-storage cavity 121 via the top end of the pre-storage cavity 121 to mix with the preservative fluid in the collection process.

As can be seen from FIGS. 1-3, in this embodiment, the outer diameter of the pre-storage tube 12*a* is smaller than the inner diameter of the storage member 2, so that the lower end of the pre-storage tube 12*a* may be inserted into the storage chamber 21 when the collection member 1 is connected to the storage member 2. Further, as shown in FIG. 3, the end surface at the lower end of the pre-storage tube 12*a* of this embodiment (i.e., the end surface at one end of the pre-storage tube 12*a* provided with the end opening 122) is provided so as to able to abut on the side wall of the aforementioned recess 13*a*. In this way, after the lower end of the pre-storage tube 12*a* protrudes into the storage chamber 21, the end surface at the lower end of the pre-storage tube 12*a* may abut on the side wall of the recess 13*a* to effectuate sealing the end opening 122, so that a first chamber 211 is formed by the lateral outer wall of the pre-storage cavity 121 and the lateral inner wall of the storage chamber 21, and a second chamber 212 is formed by the pre-storage tube 12*a* and the recess 13*a*.

And, the first chamber 211 may maintain communication with the collection port 1111 via the aforementioned outflow port disposed at the connection between the pre-storage tube 12*a* and the inner wall of the collection cavity 1112. Thus, the saliva may flow into the first chamber 211 via the collection port 1111 and the outflow port in the collection process. Moreover, owing to an abutment fit between the pre-storage tube 12*a* and the side wall of the recess 13*a*, the second chamber 212 may be isolated from the first chamber 211, and the pre-storage cavity 121 pre-stores the preservative fluid. Accordingly, after the end surface at the lower end of the pre-storage tube 12*a* abuts on the side wall of the recess 13*a*, the preservative fluid may be sealed in the second chamber 212, and isolated from the outside. On one hand, it is possible to effectuate sealing the preservative fluid before the start of the collection, so as to prevent leakage of the preservative fluid before being used (for example in the transport process). On the other hand, it is also possible to allow that the preservative fluid may be isolated from the saliva in the collection process, and prevent that both of them are mixed in the collection process.

Specifically, in this embodiment, the second chamber 212 comprises the pre-storage cavity 121 and a space of the recess 13*a* located below the abutment. After the collection member 1 is engaged with the storage member 2, a part of the preservative fluid pre-stored in the pre-storage cavity 21 in advance may still be remained in the storage cavity 121, and the other part may flow into the space of the recess 13*a* located below the abutment.

It can be seen that in the first embodiment, the storage chamber 21 is partitioned into the first chamber 211 and the second chamber 212 located inside the first chamber 211, by an abutment fit between the pre-storage tube 12*a* and the recess 13*a*, so that the preservative fluid may be sealed in the hermetic second chamber 212 to isolate the preservative fluid from the outside until it is necessary to mix the preservative fluid with the saliva. Since the abutment fit between the pre-storage tube 12*a* and the recess 13*a* may be formed along with the engagement of the collection member 1 with the storage member 2, it is only necessary to engage the collection member 1 with the storage member 2 so as to seal and isolate the preservative fluid, and it is unnecessary to add other operational steps prior to the engagement of the collection member 1 with the storage member 2. Accordingly, it is possible to more conveniently realize the expected sealing of the preservative fluid, and simplify the sealing process of the preservative fluid. Moreover, as there is no need to seal the film of the pre-storage cavity 121, the film sealing process may be omitted. Therefore, in this embodiment, such manner of forming temporary independent cavities (also i.e. a second chamber 212) in an abutment fit manner, may also simplify the machining process of the bodily fluid collector, reduce the machining difficulty and lessen the machining cost.

Moreover, since the sealing and isolation of the first chamber 211 and the second chamber 212 are formed by an abutment fit between the pre-storage tube 12a and the recess 13a, and the abutment fit between the pre-storage tube 12a and the recess 13a may be released along with the separation of the collection member 1 from the storage member 2, when the collection amount of the saliva meets the requirement, it is only necessary to separate the collection member 1 from the storage member 2, such as to release an abutment fit between the pre-storage tube 12a and the recess 13a and damage the sealing of the second chamber 212, so that the second chamber 212 communicates with the first chamber 211 located outside the same to effectuate rapidly mixing the preservative fluid with the saliva. It can be seen that, this embodiment, which effectuates sealing the preservative fluid using the temporary independent cavities (also i.e. the second chamber 212) on the basis of an abutment fit manner, not only may simplify the sealing process of the preservative fluid, but also can conveniently and rapidly release the sealing of the preservative fluid when necessary, so as to achieve the purpose of mixing the preservative fluid with the saliva and prolonging the storage duration of the DNA sample. Moreover, since there is no need to provide a structure or member such as a blade to specially damage a sealed state of the second chamber 212, the bodily fluid collector of this embodiment has less members and simpler structure, and may effectively avoid the occurrence of such a phenomenon that the bodily fluid cannot be mixed with the preservative fluid resulting from a cutting failure of the blade and the like, and improve the operational reliability of the bodily fluid collector.

In addition, in this embodiment, the second chamber 212 for sealing the preservative fluid is located inside the first chamber 211 for receiving the saliva, so that the preservative fluid may be added into the second chamber 212 in advance without having to pass through the first chamber 211, and unnecessary loss and residue of the preservative fluid in the first chamber 211 can be avoided. It is not only possible to ensure that the bodily fluid and the preservative fluid are better isolated until the completion of the collection, and it is also possible to more effectively avoid the chemical harm caused by the preservative fluid to the collected person, and improve the operational convenience and the operational safety. Moreover, the internally and externally provided second chamber 212 and first chamber 211 in this embodiment, may also allow that the saliva and the preservative fluid are both located at the bottom of the storage member 2 in the collection process (i.e. prior to the mixing), so that the saliva may more rapidly be mixed with the preservative fluid in a more thorough manner once the collection member 1 is separated from the storage member 2, thereby enabling improving the mixing efficiency and the mixing quality.

As shown in FIGS. 1-4, in this embodiment, the blockage 3 is configured to be detachably connected to the upper opening of the storage chamber 21, so as to effectuate sealing or conducting the upper opening of the storage chamber 21. When the blockage 3 is engaged with the upper opening of the storage chamber 21, the blockage 3 seals the upper opening of the storage chamber 21; when the blockage 3 is separated from the upper opening of the storage chamber 21, the upper opening of the storage chamber 21 is open. As described above, the blockage 3 is connected to the upper opening of the storage chamber 21 after the collection is completed, so that the blockage 3 may seal the mixture of the saliva and the preservative fluid to store, so as to facilitate subsequent storage and transport.

Moreover, in order to prevent such a phenomenon as the loss of the blockage 3 after being removed from the upper opening of the storage chamber 21, in this embodiment, the blockage 3 is further provided to be connectable to the lower end of the storage member 2, so that the blockage 3 may be engaged to the lower end of the storage member 2 before the start of the collection and after the completion of the collection, thereby preventing the loss of the blockage 3, and further facilitating the use of the bodily fluid collector. The detachable connection between the blockage 3 and the lower end of the storage member 2 may be realized by various connection manners such as threaded connection or snap-fit connection.

Figure 4:
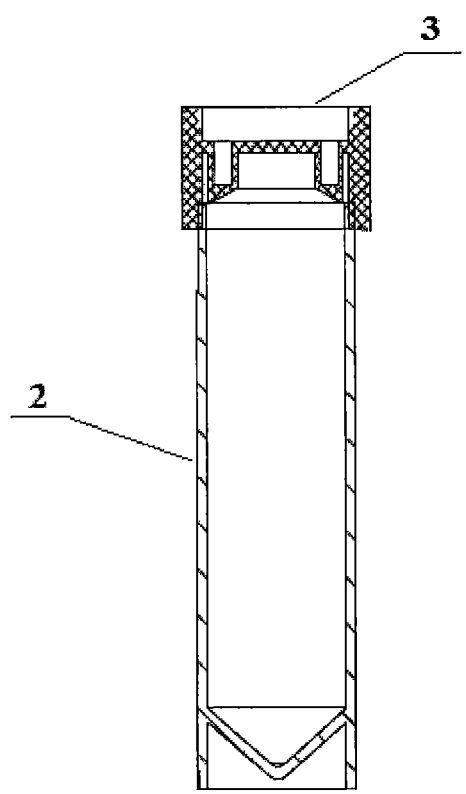
FIG. 4 shows a cross-sectional view when the blockage and the upper opening of the storage member are in a fitted state in FIG. 1.

Specifically, in combination with FIG. 3 and FIG. 4, it can be known that, in this embodiment, the blockage 3 is a double-headed cover, in which the first end of the blockage 3 is adapted to the upper end of the storage member 2, and the inner wall of the first end is provided with an internal threaded to realize a detachable connection of the blockage 3 and the storage member 2. After the first end of the blockage 3 is screwed onto the storage member 2, the first end of the blockage 3 covers the upper opening of the storage chamber 21, so that the sealing of the upper opening of the storage chamber 21 may be realized. The second end of the blockage 3 is adapted to the lower end of the storage member 2, and the second end may be connected to the lower end of the storage member 2 in a plurality of manners such as a snap-fit connection or a threaded connection.

When the saliva is collected based on the bodily fluid collector of the first embodiment, it may proceed according to the following three steps:

(1) The saliva is spat into the funnel 111 of the collection member 1 screwed on the storage member 2 so that the saliva flows into the first chamber 211 of the storage member 2 via the outflow port. Since the end surface at the lower end of the pre-storage tube 12a of the collection member 1 abuts on the side wall of the recess 13a of the storage member 2 at this time, the first chamber 211 and the second chamber 212 internally sealed with the preservative fluid are isolated from each other. Therefore, in the process, the saliva and the preservative fluid are isolated from each other without being mixed.

(2) When the collection amount of the saliva meets the requirement, for example, when the level of the saliva within the first chamber 211 reaches or approximately reaches the scale line on the storage member 2 (i.e., the collection amount reaches or approximately reaches a predetermined amount), the funnel 111 is unscrewed from the storage member 2, so that the collection member 1 is separated from the storage member 2. Since the end surface at the lower end of the pre-storage tube 12a is disengaged from the side wall of the recess 13a at this time, the second chamber 212 and the first chamber 211 outside the same communicate with each other, so that the saliva is mixed with the preservative fluid.

(3) The blockage 3 is removed from the lower end of the storage member 2 and tightened to the upper portion of the storage member 2, so that the blockage 3 seals the upper opening of the storage chamber 21.

It can be seen that, when the saliva is collected by the bodily fluid collector of the embodiment, it is only necessary to perform operation in such steps as to "spit the saliva", "unscrew the funnel 111" and "screw the blockage 3", so that there involve less steps and simpler operations, and it is easy to implement.

Of course, in order to more uniformly mix the preservative fluid with the saliva, it is also possible to provide the step (4) after step (3), i.e. shaking upside down the storage member 2 with the blockage 3 sealed at the upper portion. By shaking upside down, the preservative fluid may be further mixed with the saliva to effectuate more uniformly mixing both of them. This may not only effectively prolong the storage duration of the saliva but also facilitate the subsequent detection of the sample.

FIGS. 5-9 show a second embodiment of the bodily fluid collector according to the present disclosure. In the second embodiment, the preservative tablet A as a preservative product is taken as an example.

As shown in FIGS. 5-9, in the second embodiment, the bodily fluid collector still comprises a collection member 1, a storage member 2, and an blockage 3, and the storage chamber 21 still is partitioned into the first chamber 21 and the second chamber 22 by an abutment fit between the pre-storage structure 12 provided at the lower end of the collection member 1 and the sealing structure 13 provided on the storage member 2. Moreover, in the second embodiment, the recess 13a disposed at the bottom of the storage chamber 21 is still used as a sealing structure 13. However, different from the first embodiment, in the second embodiment, the pre-storage tube 12a is no longer used as a pre-storage structure 12. Rather, the pre-storage block 12b is used as a pre-storage structure 12, and the pre-storage cavity 121 of the pre-storage block 12b is configured to pre-store the preservative tablet A.

Figure 6:
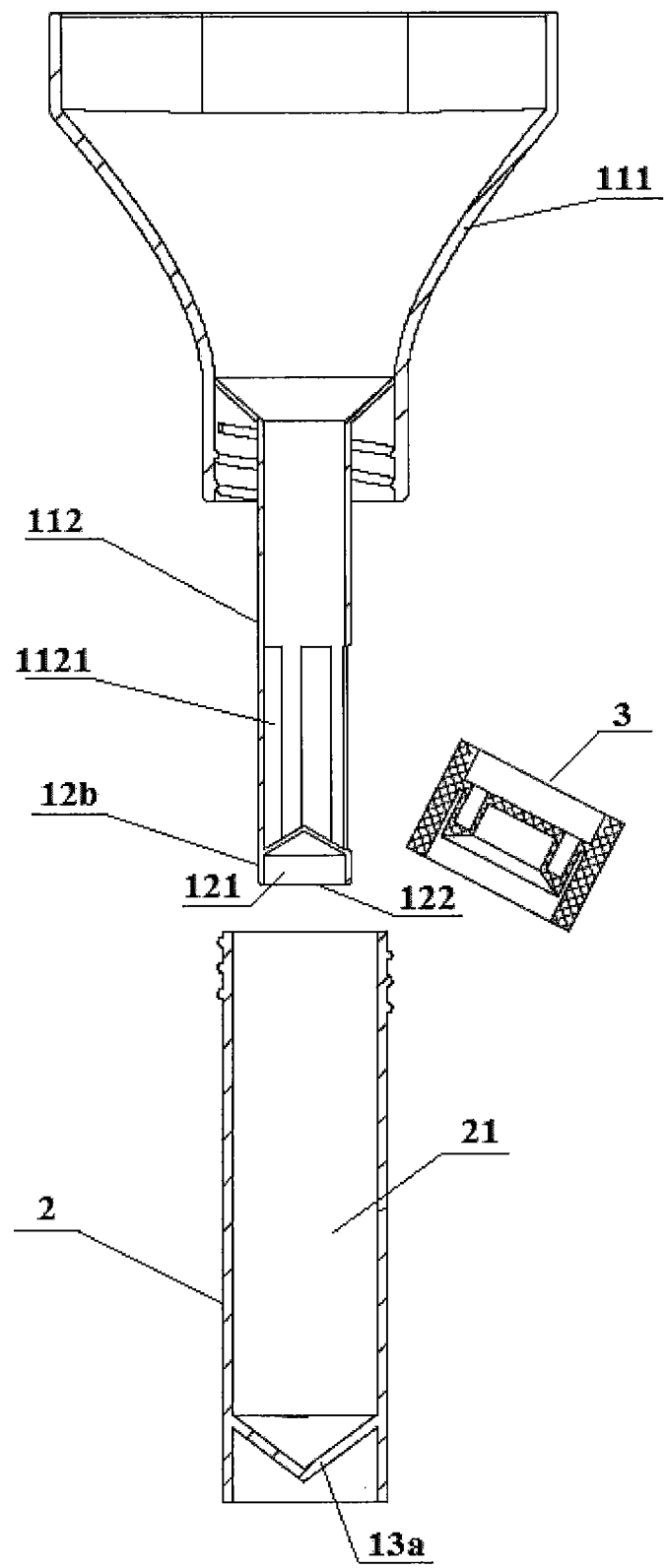
FIG. 6 shows an exploded structural view of FIG. 5.
Figure 7:
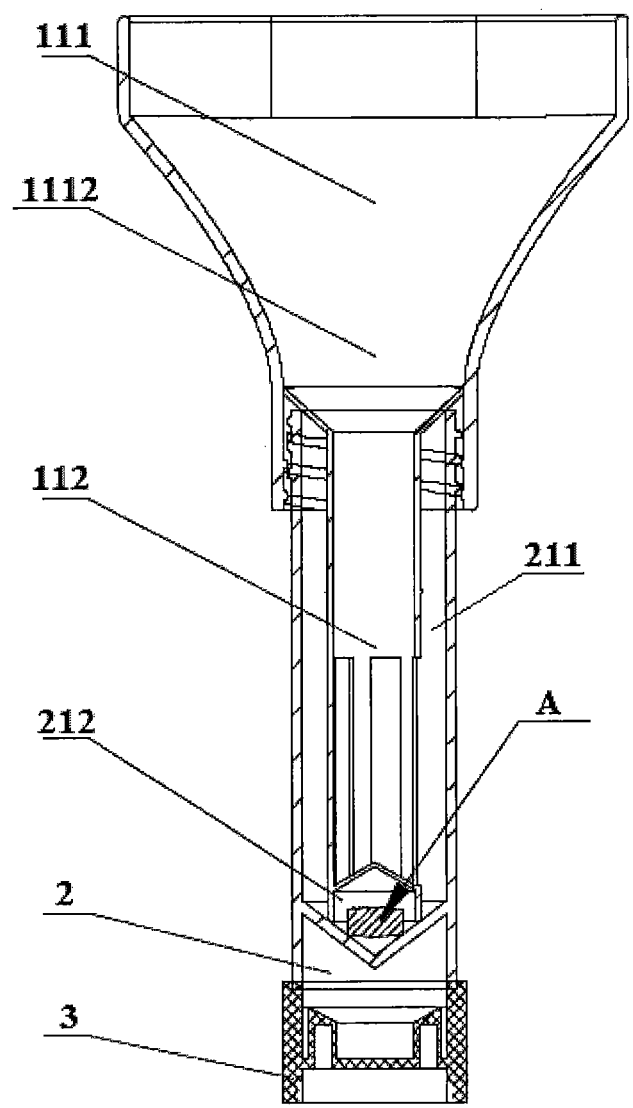
FIG. 7 shows a cross-sectional view of the bodily fluid collector shown in FIG. 5 when the collection member and the storage member are in an engaged state.
Figure 8:
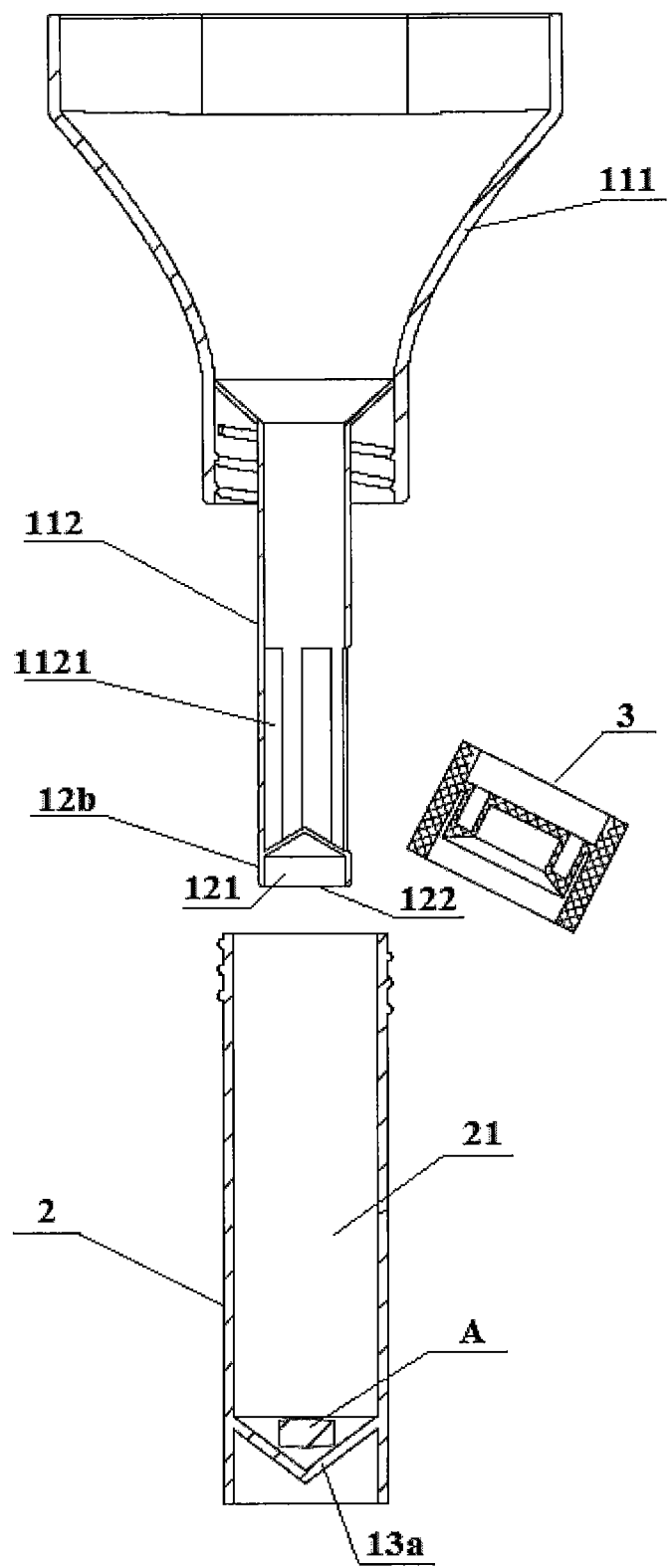
FIG. 8 shows a state view after the collection member in FIG. 7 is removed.
Figure 9:
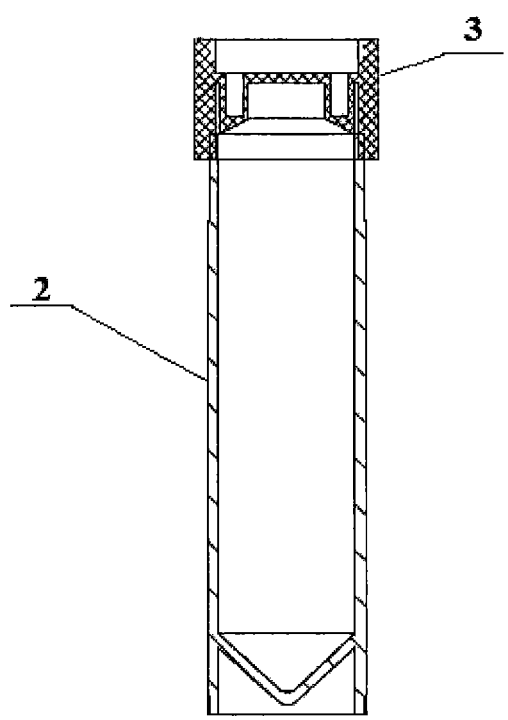
FIG. 9 shows a cross-sectional view when the blockage and the upper opening of the storage member are in a fitted state in FIG. 5.

Specifically, as shown in FIG. 6-8, in the second embodiment, the pre-storage block 12b is disposed at the lower end of the collection member 1, and the pre-storage block 12b is provided with a groove. The cavity of the groove is used as a pre-storage cavity 121 for pre-storing the preservative tablet A; the opening of the groove is used as an end opening 122 for receiving the preservative tablet A, so that the preservative tablet A can be placed into the pre-storage cavity 121 via the end opening 122. Moreover, the pre-storage block 12b is provided such that an end surface at its lower end can abut on the side wall of the recess 13a. Thus, as shown in FIG. 7, when the collection member 1 is engaged with the storage member 2, the lower end of the pre-storage block 12b abuts on the side wall of the recess 13a. It is possible to effectuate sealing the end opening 122 and form the first chamber 211 and the second chamber 212 that are temporarily independent of each other. On such basis, similar to the first embodiment, before the assembly of the collection member 1 and the storage member 2, the collection member 1 may be inverted first with the end opening 122 facing upward, and the preservative tablet A may be placed into the pre-storage cavity 121 (groove) via the end opening 122, so that the preservative tablet A is stored in the pre-storage chamber 121 in advance. Afterwards, the storage member 2 is engaged to the collection member 1, so that the recess 13a abuts on the pre-storage block 12b, to isolatedly form such a sealed temporary independent cavity as the second chamber 212, so that the preservative tablet A is isolated from the outside until it is necessary to be mixed with the saliva.

It can be seen that, the second embodiment, in which the first chamber 211 and the second chamber 212 isolated from each other can be formed by abutting the end surface at a lower end of the pre-storage block 12b with the side wall of the recess 13a, conveniently effectuates sealing and isolating the bodily fluid and the preservative tablet A in the collection process. Moreover, similar to the first embodiment, the internally and externally provided second chamber 212 and first chamber 211 according to this embodiment, also allow that the saliva and the preservative tablet A are located at the bottom of the storage member 2 in the collection process, so that the saliva may more rapidly be mixed with the preservative tablet A in a more thorough manner once the collection member 1 is separated from the storage member 2, thereby improving the mixing efficiency and the mixing quality.

Further, in order to enable the preservative tablet A to be remained in the recess 13a when the collection member 1 is separated from the storage member 2, as shown in FIGS. 7 and 8, in this second embodiment, the size of the groove is provided to be greater than that of the preservative tablet A, such that the groove is loosely fitted with the preservative tablet A. When the end opening 122 is opened downwards and the sealing is released, also namely, when the collection member 1 is upright and separated from the storage member 2, the preservative tablet A can be disengaged from the groove and remained in the recess under the effect of gravity, so as to conveniently effectuate disengaging the preservative tablet A from the pre-storage structure 12.

It should be noted that, in order to effectuate separating the preservative tablet A from the pre-storage structure 12, the present disclosure may also use other manners. For example, a push-out mechanism may also be provided on the pre-storage structure 12. The push-out mechanism is provided to enable pushing the preservative tablet A to be disengaged from the pre-storage cavity 121 and remain it in the recess 13a when the collection member 1 is separated from the storage member 2. It can be seen that, a passive disengagement of the preservative tablet A from the pre-storage structure 12 can be realized, and such manner is especially adapted to the circumstance that the pre-storage cavity 121 is in tight fit with the preservative tablet A by providing a push-out mechanism.

Figure 5:
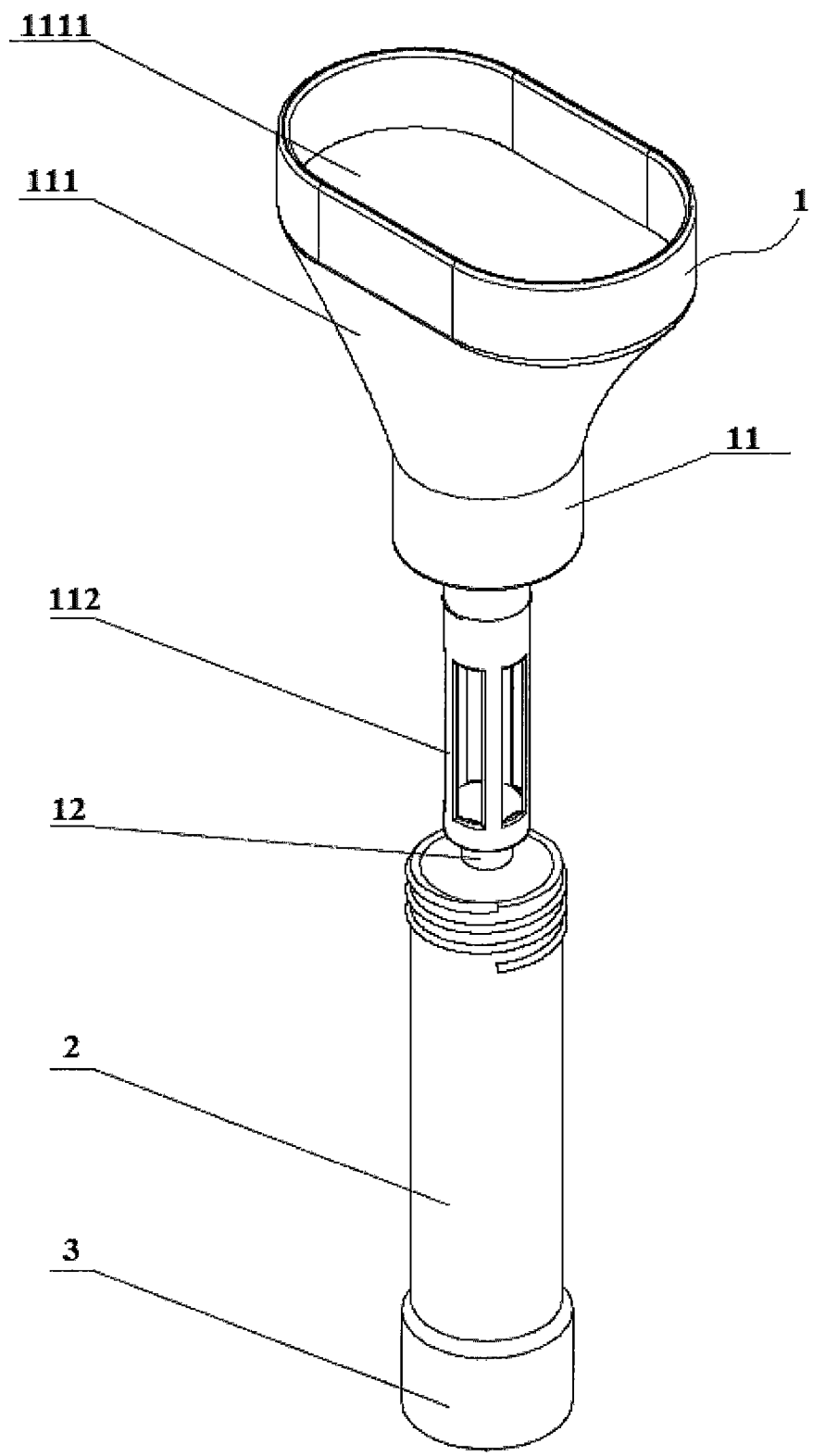
FIG. 5 shows a perspective structural view of the bodily fluid collector according to a second embodiment of the present disclosure when the collection member and the storage member are not in an engaged state.

In addition, as shown in FIG. 5-7, another main difference between the second embodiment and the first embodiment is that: in the collection member 1 of the second embodiment, the collection body 11 thereof not only comprises a funnel 111, but also comprises a conduit 112. Specifically, as shown in FIG. 6 and FIG. 8, in the second embodiment, the conduit 112 is connected between the funnel 111 and the pre-storage block 12 b. Also in other words, the conduit 112 is connected between the upper end and the lower end of the collection member 1, so that the pre-storage structure 12 of this embodiment is no longer directly connected to the inner wall of the collection cavity 1112, but connected to the inner wall of the collection cavity 1112 through the conduit 112. Moreover, at least part of the upper end of the conduit 112 communicates with the collection port 1111 (i.e. the upper end of the collection member 1), and at the same time, the lower end of the conduit 112 is enclosed, with an opening 1121 provided on the side wall of the conduit 112. When the collection member 1 is engaged with the storage member 2, the conduit 112 protrudes into the storage chamber 21, so that the first chamber 211 communicates with the collection port 1111 through the opening 1121. Thereby, in the saliva collection process, the saliva may enter the conduit 112 via the collection port 1111, and flow into the first chamber 211 via the opening 1121, to effectuate collecting the saliva and maintaining that the collected saliva is isolated from the preservative tablet A sealed in the second chamber 212. It can be seen that, the saliva may be guided to flow more smoothly so as to further improve the bodily fluid collection efficiency by providing the conduit 112. Moreover, in this embodiment, the function of the conduit 112 also lies in that a support is formed for the pre-storage block so as to enable the pre-storage block 12b to abut on the side wall of the recess 13a more conveniently.

When the saliva is collected based on the bodily fluid collector of the second embodiment, it may proceed according to the following three steps:

(1) The saliva is spat into the funnel 111 of the collection member 1 screwed on the storage member 2 so that the saliva flows into the first chamber 211 of the storage member 2 via the opening 1121 on the side wall of the conduit 112. Since the end surface at the lower end of the pre-storage tube 12b abuts on the side wall of the recess 13a of the storage member 2 at this time, the first chamber 211 and the second chamber 212 internally sealed with the preservative tablet A are isolated from each other. Therefore, in the process, the saliva and the preservative tablet A are isolated from each other without being mixed.

(2) When the collection amount of the saliva meets the requirement, the funnel 111 is unscrewed from the storage member 2, so that the collection member 1 is separated from the storage member 2. Since the end surface at the lower end of the pre-storage block 12b is disengaged from the side wall of the recess 13a at this time, the second chamber 212 and the first chamber 211 outside the same communicate with each other, and the preservative tablet A is remained in the recess 13a under the effect of gravity, so that the saliva is mixed with the preservative tablet A for reaction.

(3) The blockage 3 is removed from the lower end of the storage member 2 and tightened to the upper portion of the storage member 2, so that the blockage 3 seals the upper opening of the storage chamber 21.

It can be seen that, when the saliva is collected by the bodily fluid collector of the second embodiment, it is also only necessary to perform operation in such steps as to "spit the saliva", "unscrew the funnel 111" and "screw the blockage 3", so that there involve less steps and simpler operations, and it is easy to implement.

Of course, similar to the first embodiment, in order to more uniformly mix the preservative tablet A with the saliva, it is also possible to provide the step (4) after step (3), i.e. shaking upside down the storage member 2 with the blockage 3 sealed at the upper portion.

The recesses 13a of the first embodiment and the second embodiment each present an inverted conical shape, and the recess 13a using this shape abuts on the pre-storage structure 12. The advantages thereof lie in that, on one hand, the recess 13a may be fitted with the pre-storage structure 12 to effectuate a more tight sealing of the second chamber 212; and on the other hand, since a recess 13a in an inverted conical shape is normally provided at the bottom of the storage chamber 21 of the existing storage member 2, it is possible to directly utilize the recess 13a on the existing storage member 2 to abut on the pre-storage structure 12, such as to sealingly and isolatingly form the second chamber 212 under the premise of not having to change the structure of the existing storage member 2, thereby enabling further simplifying the structure, reducing the machining difficulty and lessening the machining cost. However, it should be understood that, the recess 13a may also adopt other variable cross-sectional structure such as a hemispherical shape as long as its variable cross-section can abut on one end of the pre-storage structure 12 provided with an end opening 122 to realize the sealing.

In addition, although in the first embodiment and the second embodiment, the pre-storage structures 12 are disposed at the lower end of the collection member 1, and correspondingly, the sealing structures 13 are disposed on the storage member 2 and located in the storage chamber 21. However, as a matter of fact, the configuration positions of the pre-storage structure 12 and the sealing structure 13 may also be interchanged. That is, the pre-storage structure 12 may also be disposed on the storage member 2 and located in the storage chamber 21. Correspondingly, the sealing structure 13 may also be disposed at the lower end of the collection member 1. The third embodiment shown in FIGS. 10-13 shows such an embodiment.

As shown in FIGS. 10-13, in the third embodiment, the pre-storage structure 12 adopts a pre-storage tube 12a, which is disposed in the storage chamber 21, with its upper end open and the lower end enclosed, i.e., the end opening 122 is located at the upper end of the pre-storage cavity 121. The sealing structure 13 adopts a sealing gasket 13b, which is disposed at the lower end of the collection member 1. Specifically, the sealing gasket 13b is connected to the inner wall of the funnel 111 through a support body 14. On such basis, the preservative fluid may be pre-stored in the cavity of the pre-storage tube 12a provided on the storage member 2, and then the collection member 1 is engaged to the storage member 2, so that the sealing gasket 13b is attached to and pressed against the end surface at the upper end of the pre-storage tube 12a (i.e., the end surface at one end of the pre-storage tube 12a provided with the end opening 122), so as to effectuate sealing the end opening 122, and the storage chamber 21 is partitioned into a first chamber 211 and a second chamber 212 which are isolated from each other. As can be known from FIG. 11, the upper and lower ends of the support body 14 of this embodiment are both closed, and in order to achieve the communication between the first chamber 211 and the collection port 1111, an outflow port is provided at the connection between the support body 14 and inner wall of the collection cavity 1112, such that the saliva may flow into the first chamber 211 outside the second chamber 212 via the collection port 1111 and the outflow port when the collection member 1 is engaged to the storage member 2 to collect the saliva. Certainly, as an alternative embodiment, the support body 14 may also adopt the structure of the conduit 112 in the second embodiment. That is, the support body 14 is provided to be a hollow tube structure, with an upper end open, a lower end enclosed and a side wall provided with an opening 1121, so as to effectuate communicating the first chamber 211 with the collection port 1111.

Figure 10:
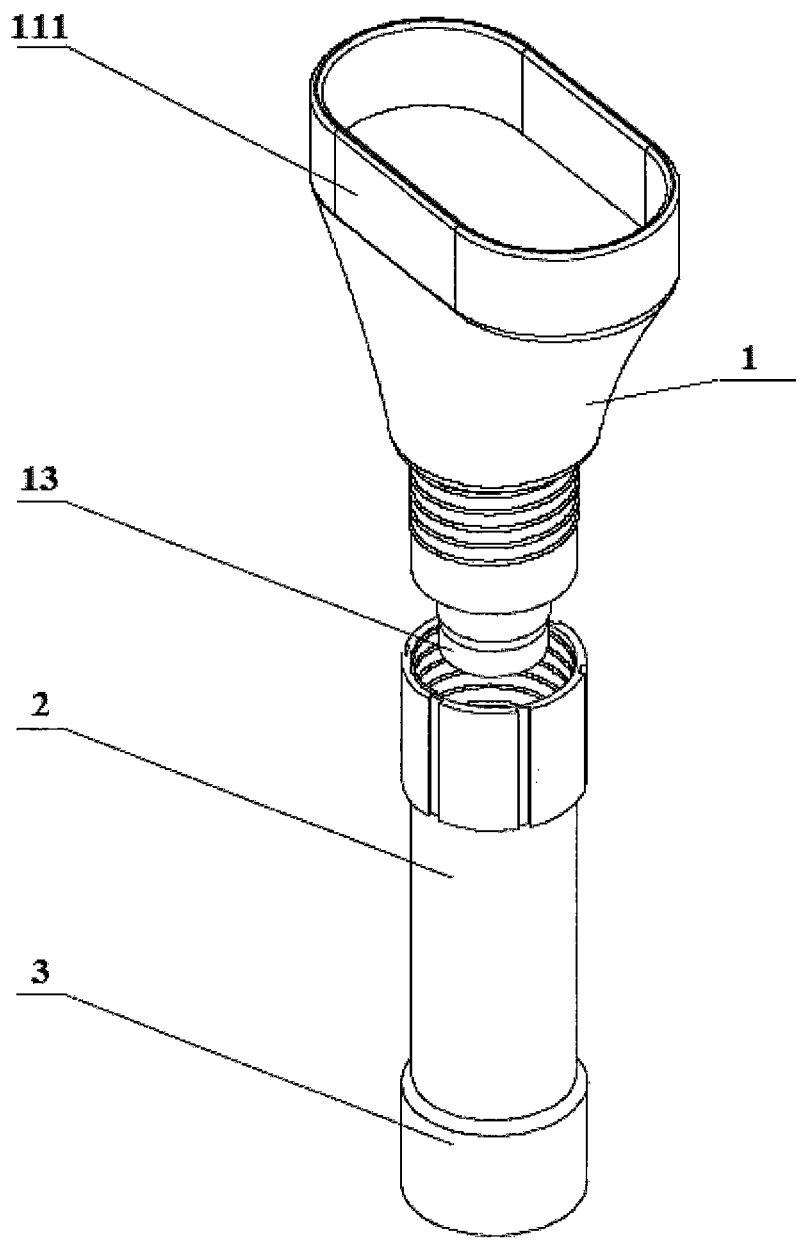
FIG. 10 shows a perspective structural view of the bodily fluid collector according to a third embodiment of the present disclosure when the collection member and the storage member are not in an engaged state.
Figure 11:
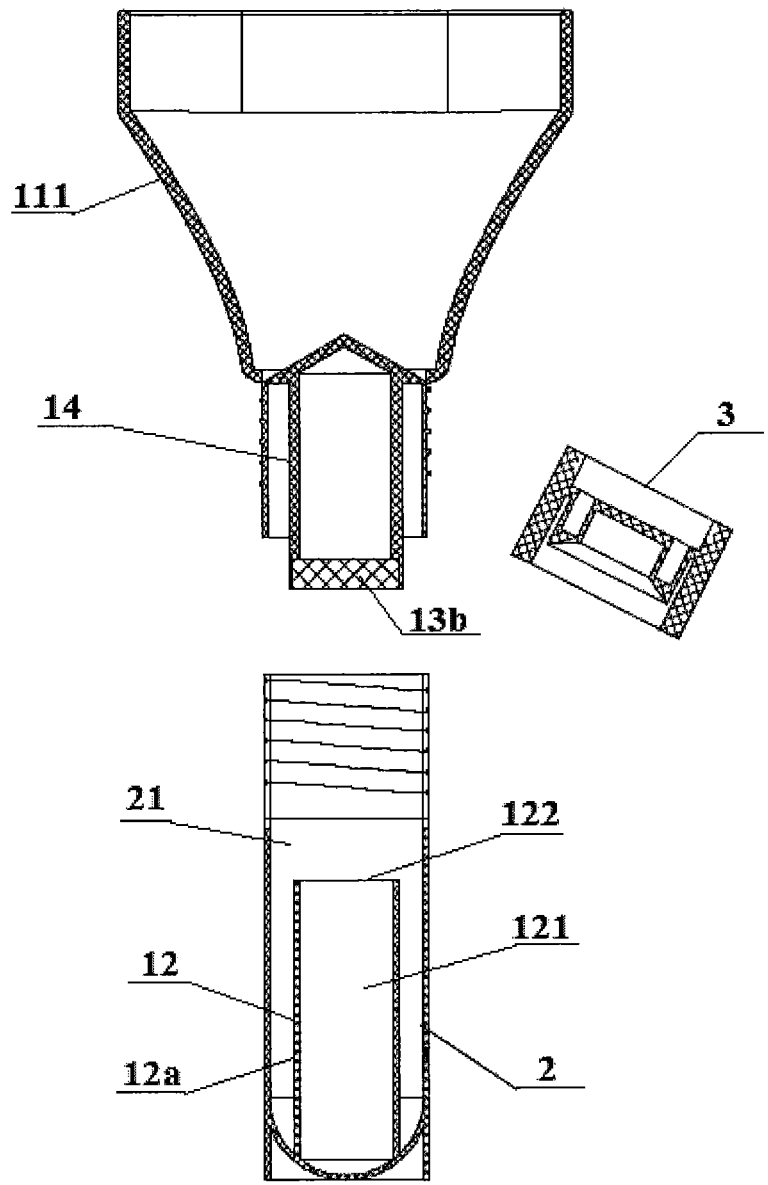
FIG. 11 shows an exploded structural view of FIG. 10.
Figure 12:
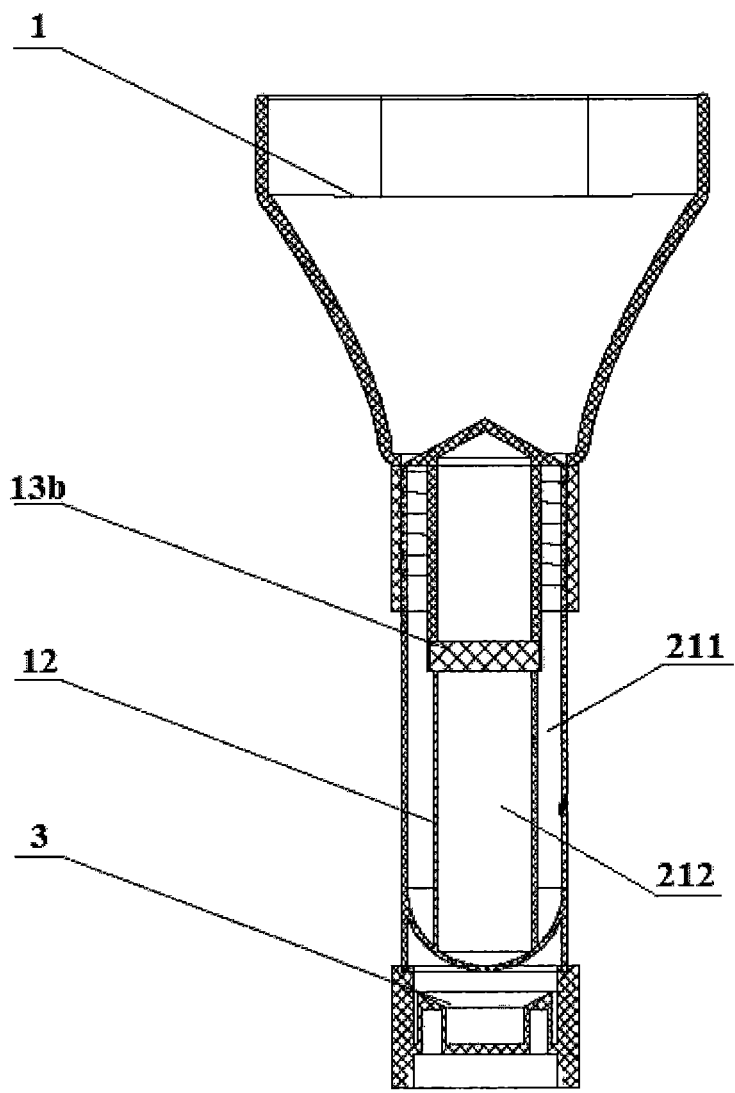
FIG. 12 shows a cross-sectional view of the bodily fluid collector shown in FIG. 10 when the collection member and the storage member are in an engaged state.
Figure 13:
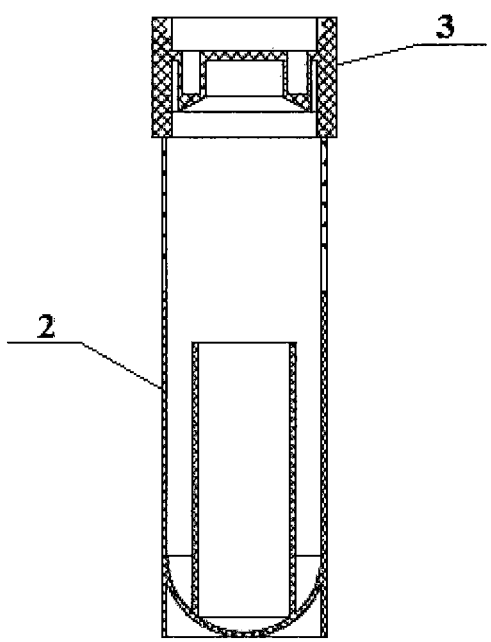
FIG. 13 shows a cross-sectional view when the blockage and the upper opening of the storage member are in a fitted state in FIG. 10.

In addition, as can be known from FIGS. 10-12, the difference between the third embodiment and the first two embodiments further lies in that, in the third embodiment, the thread on the storage member 2 no longer adopts an external thread but an internal thread. That is, the thread is disposed on the upper portion of the inner wall of the storage chamber 21. Correspondingly, the thread on the collection cavity 1112 no longer adopts an internal thread, but an external thread provided on the outer wall of the collection cavity 1112. A threaded connection manner is used to connect the collection member 1 and the storage member 2 to effectuate detachably connecting the collection member 1 with the storage member 2, thereby not only facilitating that a user engages and disengages the collection member 1 and the storage member 2, but also facilitating that the sealing gasket 13b more closely covers the end opening 122, so as to effectuate a more tight sealing of the end opening 122.

When the saliva is collected based on the bodily fluid collector of the third embodiment, it may proceed according to the following three steps:

(1) The saliva is spat into the funnel 111 of the collection member 1 screwed on the storage member 2 so that the saliva flows into the first chamber 211 of the storage member 2 via the outflow port. Since the sealing gasket 13b at the lower end of the collection member is attached to and pressed against the end surface at the upper end of the pre-storage tube 12a in the storage chamber 2 at this time, the first chamber 211 and the second chamber 212 internally sealed with the preservative fluid are isolated from each other. Therefore, in the process, the saliva and the preservative fluid are isolated from each other without being mixed.

(2) When the collection amount of the saliva meets the requirement, the funnel 111 is unscrewed from the storage member 2, so that the collection member 1 is separated from the storage member 2. Since the sealing gasket 13b is disengaged from the end surface at the upper end of the pre-storage tube 12a, the second chamber 212 and the first chamber 211 outside the same communicate with each other.

(3) The blockage 3 is removed from the lower end of the storage member 2 and tightened to the upper portion of the storage member 2, so that the blockage 3 seals the upper opening of the storage chamber 21, and then the storage member 2 is inverted. As the second chamber 212 has communicated with the first chamber 211 outside the same in the step (2), after the storage member 2 is inverted, the preservative fluid stored in the pre-storage tube 12a may flow out from the end opening 122 to mix with the collected saliva.

It can be seen that, when the saliva is collected by the bodily fluid collector of the third embodiment, it is also only necessary to perform operation in such steps as to "spit the saliva", "unscrew the funnel 111" and "screw the blockage 3 and invert the storage member 2", so that there involve less steps and simpler operations, and it is easy to implement.

Of course, similar to the first two embodiments, in order to more uniformly mix the preservative fluid with the saliva, it is also possible to provide the step (4) after step (3), i.e. shaking upside down the storage member 2 with the blockage 3 sealed at the upper portion.

Based on the aforementioned three embodiments, it may be seen that these three embodiments all use the collection port 1111 of the funnel 111 to directly collect the saliva, that is, the collected person voluntarily spits the saliva into the funnel 111 to complete the collection of the saliva. Such saliva collection manner is more suitable for adults, especially suitable for the circumstance that there is a great predetermined collection amount of the saliva. However, for the collected person such as the elderly or children, who are not likely to voluntarily complete or not likely to better complete spitting the saliva into the funnel 111, or for the circumstance that there is less predetermined collection amount, it is more appropriate to use another saliva collection manner.

Figure 14:
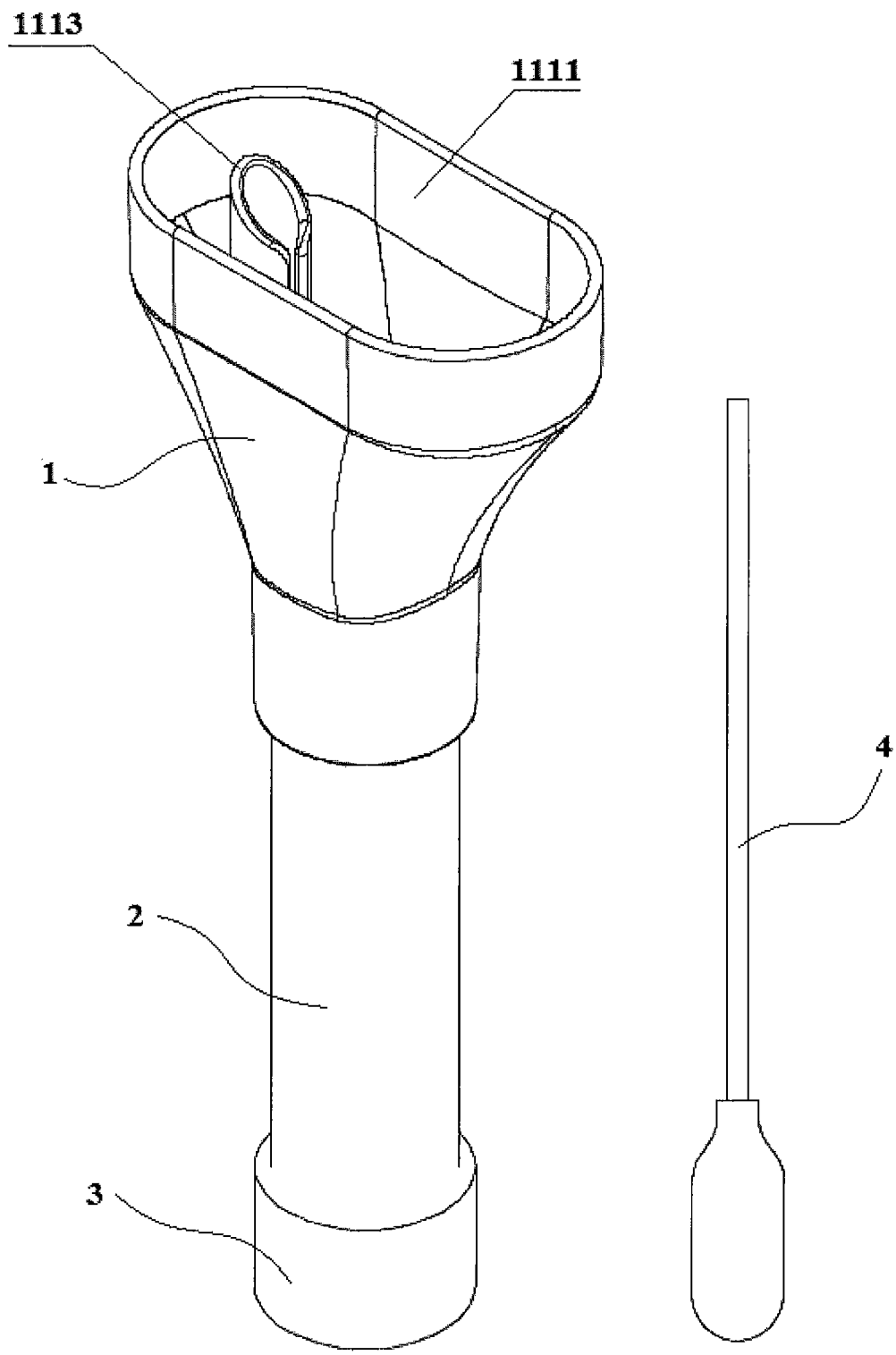
FIG. 14 shows an overall structural view of the bodily fluid collector according to a fourth embodiment of the present disclosure.

Therefore, the present disclosure also provides a fourth embodiment as shown in FIG. 14. The fourth embodiment may still use any manner of the aforementioned three embodiments to partition the storage chamber 21 into the first chamber 211 and the second chamber 212. However, in order to be adapted more to the collected person such as the elderly or the children or be adapted more to the collection demand of a small amount of sample, the fourth embodiment no longer directly utilizes the funnel 111 to collect the saliva spat by the collected person, but utilizes such a sampling member as a cotton swab 4 for protruding into the mouth of the collected person to dip the saliva, so as to achieve collection of the saliva. Under such circumstance, in order to facilitate smoothly flowing the saliva dipped on such a sampling member as a cotton swab 4 into the storage member 2 to measure the collection amount and mix with the preservative product, as shown in FIG. 14, the bodily fluid collector may also comprise a liquid squeezing tank 1113 provided on the collection member 1. The liquid squeezing tank 1113 is used for squeezing the sampling member dipped with the saliva and guiding the squeezed saliva into the first chamber 211. Specifically, it can be known from FIG. 14 that, the liquid squeezing tank 1113 of the fourth embodiment is connected to the inner wall of the collection cavity 1112, its both ends are open, and the upper opening is adapted to one end of the cotton swab 4 provided with a cotton tip, so that one end of the cotton swab 4 provided with a cotton tip may protrude into the liquid squeezing tank 1113. On such basis, during the collection, one end of the cotton swab 4 provided with a cotton tip may be protruded into the inside of the cheek of the collected person, to reciprocally wipe the inside of the cheek and the root of the gingival, so that a proper amount of saliva is dipped on the cotton tip of the cotton swab 4. Then, the cotton swab 4 is removed from the mouth and inserted into the liquid squeezing tank 1113, and the cotton tip is squeezed with the inner wall of the liquid squeezing tank 1113, to squeezing the saliva out. Moreover, the saliva is made to flow downward into the first chamber 211 along the inner wall of the liquid squeezing tank 1113, to effectuate effectively collecting the saliva.

Based on the aforementioned four embodiments, it may be seen that, the bodily fluid collector of the present disclosure utilizes the fit between the lower end of the collection member 1 and the storage member 2 to enable that the bodily fluid collection area (i.e., the first chamber 211) and the preservative product storage area (the second chamber 212) are isolated until the collection amount satisfies the requirements that not only there are less operational steps and high collection efficiency, but also there are less amount of parts with a simple process and a less difficult machining, so that it is more likely to realize automatic production and facilitate controlling the production cost after a large-scale industrial mass production. Moreover, with a highly reliable operation, the user's experience can be effectively improved.

In addition, it should be noted that, although in the aforementioned four embodiments, the storage member 2, the pre-storage tube 12a, and the conduit 112 are all circular tube structures, those skilled in the art should understand that, in fact, they can also be a square tube structure or a tube structure of other cross-sectional shapes, and even profiled tubes may be used. These are all within the protection scope of the present disclosure. Further, the circular tube structure used in the aforementioned four embodiments, has the advantages of facilitating the machining and facilitating the use.

Based on the bodily fluid collector of the present disclosure, the present disclosure also provides a bodily fluid collection method. The bodily fluid collection method comprises the following steps:

collecting a bodily fluid with the collection member 1 engaged to the storage member 2, such that the bodily fluid flows into the first chamber 211 that is isolated from the second chamber 212; and separating the collection member 1 and the storage member 2 when a collection amount of the bodily fluid meets the requirement, such that the first chamber 211 communicates with the second chamber 212 to mix the bodily fluid with the preservative product.

The bodily fluid collection method may further comprise: shaking the storage member 2 so that the bodily fluid and the preservative product are uniformly mixed, after the upper opening of the storage chamber 21 is sealed with the blockage 3.

The foregoing is intended only as an exemplary of the present disclosure, but is not used for limiting the present disclosure. Any amendment, equivalent replacement, improvement, and the like within the spirit and principles of the present disclosure should all be contained within the protection scope of the present disclosure.

The invention claimed is:

1. A bodily fluid collection method comprising the following steps in sequence:
    providing a bodily fluid collector, comprising a collection member, a storage member and a preservative product for preserving bodily fluid;
    wherein an upper end of the collection member is open to collect bodily fluid to be detected, and the storage member has a storage chamber for storing the collected bodily fluid;
    wherein the collection member and the storage member are configured to be separably engaged such that:
    when the collection member is engaged with the storage member, a lower end of the collection member is inserted into the storage chamber and divides the storage chamber into a first chamber and a second chamber by fitting with the storage member, wherein the first chamber communicates with the upper end of the collection member to receive the collected bodily fluid, the second chamber stores the preservative product for preserving bodily fluid and is sealedly isolated from the first chamber to isolate the bodily fluid from the preservative product; and
    when the collection member is separated from the storage member, the lower end of the collection member is released from fitting with the storage member, and the first chamber and the second chambers communicate with each other to mix the bodily fluid and the preservative product;
    wherein the second chamber is located inside the first chamber in a direction parallel to a cross section of the storage chamber;
    collecting the bodily fluid with the collection member engaged to the storage member, such that the bodily fluid flows into the first chamber isolated from the second chamber; and
    separating the collection member from the storage member when a collection amount of the bodily fluid reaches a predetermined amount, such that the first chamber communicates with the second chamber to mix the bodily fluid with the preservative product.

2. The bodily fluid collection method according to claim 1,
    wherein the bodily fluid collector further comprises a blockage, which is detachably connected to an upper opening of the storage chamber, such that the blockage seals the upper opening of the storage chamber when the blockage is fitted with the upper opening of the storage chamber;
    the bodily fluid collection method further comprising:
    shaking the storage member so that the bodily fluid and the preservative product are uniformly mixed, after the upper opening of the storage chamber is sealed with the blockage.

3. The bodily fluid collection method according to claim 1,
    wherein the lower end of the collection member is provided with a pre-storage structure, and the storage member is provided with a sealing structure, wherein the pre-storage structure comprises a pre-storage cavity for pre-storing the preservative product and an end opening located at an end of the pre-storage cavity and for receiving the preservative product into the pre-storage cavity;
    when the collection member is engaged with the storage member, the sealing structure cooperates with the pre-storage structure to seal the end opening, such that the first chamber is formed by a lateral outer wall of the pre-storage cavity and a lateral inner wall of the storage chamber, and such that the second chamber is formed by the pre-storage structure and the sealing structure;
    wherein the pre-storage structure comprises a pre-storage tube, and the pre-storage cavity is a cavity of the pre-storage tube;
    the preservative product is preservative fluid;
    wherein the sealing structure comprises a recess with a variable cross-section, wherein a side wall with a variable cross-section of the recess abuts on an end surface at one end of the pre-storage structure provided with the end opening to cover the end opening;
    wherein the bodily fluid collector further comprises a blockage, which is detachably connected to an upper opening of the storage chamber, such that the blockage seals the upper opening of the storage chamber when the blockage is fitted with the upper opening of the storage chamber;
    the bodily fluid collection method further comprising:
    performing the step of collecting the bodily fluid with the collection member engaged on the storage member so that the bodily fluid flows into the first chamber of the storage member, wherein the end surface at the lower end of the pre-storage tube of the collection member abuts on the side wall of the recess of the storage member, the first chamber and the second chamber internally sealed with the preservative fluid are isolated from each other, so that the bodily fluid and the preservative fluid are isolated from each other without being mixed;
    performing the step of separating the collection member from the storage member, when the collection amount of the bodily fluid reaches the predetermined amount, wherein the end surface at the lower end of the pre-storage tube is disengaged from the side wall of the recess, the second chamber and the first chamber outside the second chamber communicate with each other, so that the bodily fluid is mixed with the preservative fluid; and
    tightening the blockage to the upper portion of the storage member, so that the blockage seals the upper opening of the storage chamber.

4. The bodily fluid collection method according to claim 1,
    wherein the lower end of the collection member is provided with a pre-storage structure, and the storage member is provided with a sealing structure, wherein the pre-storage structure comprises a pre-storage cavity for pre-storing the preservative product and an end opening located at an end of the pre-storage cavity and for receiving the preservative product into the pre-storage cavity;

when the collection member is engaged with the storage member, the sealing structure cooperates with the pre-storage structure to seal the end opening, such that the first chamber is formed by a lateral outer wall of the pre-storage cavity and a lateral inner wall of the storage chamber, and such that the second chamber is formed by the pre-storage structure and the sealing structure;

the pre-storage structure comprises a pre-storage block having a groove, and the pre-storage cavity is a cavity of the groove, and an opening of the groove is as the end opening;

the preservative product is a preservative tablet;

wherein the sealing structure comprises a recess with a variable cross-section, wherein a side wall with a variable cross-section of the recess abuts on an end surface at one the end of the pre-storage structure provided with the end opening to cover the end opening;

wherein the collection member comprises a conduit connected between an upper end and the lower end of the collection member, wherein at least part of a upper end of the conduit communicates with the upper end of the collection member, and a lower end of the conduit is enclosed, and a side wall of the conduit is provided with an opening; the conduit protrudes into the storage chamber so that the collected bodily fluid flows into the first chamber via the opening when the collection member is engaged with the storage member;

wherein the pre-storage block is connected to the lower end of the conduit;

wherein the bodily fluid collector further comprises a blockage, which is detachably connected to an upper opening of the storage chamber, such that the blockage seals the upper opening of the storage chamber when the blockage is fitted with the upper opening of the storage chamber;

the bodily fluid collection method further comprising:

performing the step of collecting the bodily fluid with the collection member engaged on the storage member so that the bodily fluid flows into the first chamber of the storage member via the opening on the side wall of the conduit, wherein an end surface at a lower end of the pre-storage block abuts on the side wall of the recess of the storage member, the first chamber and the second chamber internally sealed with the preservative tablet are isolated from each other, so that the bodily fluid and the preservative tablet are isolated from each other without being mixed;

performing the step of separating the collection member from the storage member, when the collection amount of the bodily fluid reaches the predetermined amount, wherein the end surface at the lower end of the pre-storage block is disengaged from the side wall of the recess, the second chamber and the first chamber outside the second chamber communicate with each other, and the preservative tablet is remained in the recess under the effect of gravity, so that the bodily fluid is mixed with the preservative tablet for reaction; and tightening the blockage to the upper portion of the storage member, so that the blockage seals the upper opening of the storage chamber.

5. The bodily fluid collection method according to claim 1, wherein the storage member is provided with a pre-storage structure, and the lower end of the collection member is provided with a sealing structure, wherein the pre-storage structure comprises a pre-storage cavity for pre-storing the preservative product and an end opening located at an end of the pre-storage cavity and for receiving the preservative product into the pre-storage cavity;

when the collection member is engaged with the storage member, such that the first chamber is formed by a lateral outer wall of the pre-storage cavity and a lateral inner wall of the storage chamber, and such that the second chamber is formed by the pre-storage structure and the sealing structure;

wherein the pre-storage structure comprises a pre-storage tube, and the pre-storage cavity is a cavity of the pre-storage tube;

wherein the preservative product is preservative fluid;

wherein the sealing structure comprises a gasket which is attached to and pressed against an end surface at one end of the pre-storage structure provided with the end opening to cover the end opening, the gasket is provided at the lower end of the collection member;

wherein the bodily fluid collector further comprises a blockage, which is detachably connected to an upper opening of the storage chamber, such that the blockage seals the upper opening of the storage chamber when the blockage is fitted with the upper opening of the storage chamber;

the bodily fluid collection method further comprising:

performing the step of collecting the bodily fluid with the collection member engaged on the storage member so that the bodily fluid flows into the first chamber of the storage member, wherein the sealing gasket at the lower end of the collection member is attached to and pressed against the end surface at the upper end of the pre-storage tube in the storage chamber, the first chamber and the second chamber internally sealed with the preservative fluid are isolated from each other, so that the bodily fluid and the preservative fluid are isolated from each other without being mixed;

performing the step of separating the collection member from the storage member, when the collection amount of the bodily fluid reaches the predetermined amount, wherein the sealing gasket is disengaged from the end surface at the upper end of the pre-storage tube, so that the second chamber and the first chamber outside the second chamber communicate with each other; and tightening the blockage to the upper portion of the storage member, so that the blockage seals the upper opening of the storage chamber, and then inverting the storage member so that the preservative fluid stored in the pre-storage tube flows out from the end opening to mix with the collected bodily fluid.

\* \* \* \* \*

UNITED STATES PATENT AND TRADEMARK OFFICE
CERTIFICATE OF CORRECTION

| | | |
|---|---|---|
| PATENT NO. | : 12,408,896 B2 | Page 1 of 1 |
| APPLICATION NO. | : 16/334181 | |
| DATED | : September 9, 2025 | |
| INVENTOR(S) | : Zhan et al. | |

It is certified that error appears in the above-identified patent and that said Letters Patent is hereby corrected as shown below:

In the Claims

Column 25, Line 20, Claim 4: Please correct "surface at one the" to read --surface at the--

Signed and Sealed this
Twenty-fifth Day of November, 2025

John A. Squires
*Director of the United States Patent and Trademark Office*